(12) United States Patent
Lampropoulos et al.

(10) Patent No.: US 11,344,318 B2
(45) Date of Patent: May 31, 2022

(54) INFLATABLE RADIAL ARTERY COMPRESSION DEVICE

(71) Applicant: Merit Medical Systems, Inc., South Jordan, UT (US)

(72) Inventors: Fred Lampropoulos, Salt Lake City, UT (US); Blaine Johnson, Riverton, UT (US); Tyler Rees, Draper, UT (US); Kenneth Sykes, Bluffdale, UT (US); Randy Boyd, Riverton, UT (US); Tamara L. Newren, Saratoga Springs, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 16/921,343

(22) Filed: Jul. 6, 2020

(65) Prior Publication Data
US 2021/0052282 A1   Feb. 25, 2021

Related U.S. Application Data

(62) Division of application No. 15/648,110, filed on Jul. 12, 2017, now Pat. No. 10,702,281.
(Continued)

(51) Int. Cl.
*A61B 17/12*   (2006.01)
*A61B 17/135*   (2006.01)
(Continued)

(52) U.S. Cl.
CPC ........ *A61B 17/135* (2013.01); *A61B 17/1325* (2013.01); *A61B 17/1355* (2013.01);
(Continued)

(58) Field of Classification Search
CPC .............. A61B 17/135; A61B 17/1325; A61B 17/1355; A61B 2017/00119;
(Continued)

(56) References Cited

U.S. PATENT DOCUMENTS

| 2,547 | A | 4/1842 | Welchman |
|---|---|---|---|
| 11,623 | A | 8/1854 | Waters |

(Continued)

FOREIGN PATENT DOCUMENTS

| CA | 2546434 | 1/2013 |
|---|---|---|
| CN | 201205292 | 3/2009 |

(Continued)

OTHER PUBLICATIONS

Notice of Allowance dated Nov. 25, 2020 for U.S. Appl. No. 29/653,828.
(Continued)

*Primary Examiner* — Erich G Herbermann
(74) *Attorney, Agent, or Firm* — Dorsey & Whitney LLP

(57) ABSTRACT

Radial artery compression devices with an inflatable chamber and a substantially rigid frame are disclosed. The inflatable chamber of the radial artery compression devices can be inflated and then deflated according to a predetermined protocol. Some substantially rigid frames can form a wall of the inflatable chamber. Some substantially rigid frames can include indicia to facilitate positioning of the inflatable chamber relative to a puncture site of a patient.

15 Claims, 7 Drawing Sheets

Related U.S. Application Data

(60) Provisional application No. 62/363,695, filed on Jul. 18, 2016.

(51) Int. Cl.
*A61B 17/132* (2006.01)
*A61B 17/00* (2006.01)

(52) U.S. Cl.
CPC ............ *A61B 2017/00119* (2013.01); *A61B 2017/00199* (2013.01); *A61B 2017/00221* (2013.01); *A61B 2017/00442* (2013.01); *A61B 2017/00544* (2013.01); *A61B 2017/00734* (2013.01); *A61B 2017/00907* (2013.01)

(58) Field of Classification Search
CPC .......... A61B 2017/00221; A61B 2017/00442; A61B 2017/00544; A61B 2017/00734; A61B 2017/00907; A61B 17/12; A61B 5/02233; A61F 2013/00468; A61F 2013/0028
See application file for complete search history.

(56) References Cited

U.S. PATENT DOCUMENTS

| | | |
|---|---|---|
| 44,843 A | 10/1864 | Smith |
| 1,177,208 A | 3/1916 | Pierpont |
| 1,197,232 A | 9/1916 | Pierpont |
| 1,281,653 A | 10/1918 | Plummer |
| 2,332,107 A | 10/1943 | Nieburgs |
| 2,397,257 A | 3/1946 | Goland |
| 3,003,500 A | 10/1961 | Barton et al. |
| 3,021,841 A | 2/1962 | Burke |
| 3,050,064 A | 8/1962 | Moore et al. |
| 3,058,627 A | 10/1962 | Eskridge |
| 3,115,138 A | 12/1963 | McElvenny et al. |
| 3,233,610 A | 2/1966 | Wade |
| 3,241,554 A | 3/1966 | Coanda |
| 3,253,594 A | 5/1966 | Matthews |
| 3,312,221 A | 4/1967 | Overment |
| 3,315,802 A | 4/1967 | Lonholdt et al. |
| 3,319,684 A | 5/1967 | Calhoun |
| 3,340,869 A | 9/1967 | Bane |
| 3,363,626 A | 1/1968 | Bidwell et al. |
| 3,376,868 A | 4/1968 | Mondiadis |
| 3,417,750 A | 12/1968 | Carson |
| 3,419,010 A | 12/1968 | Williamson |
| 3,459,189 A | 8/1969 | Alley |
| 3,487,837 A | 1/1970 | Petersen |
| 3,542,026 A | 11/1970 | Bledsoe |
| 3,554,580 A | 1/1971 | Goyke |
| 3,566,875 A | 3/1971 | Stoehr |
| 3,572,340 A | 3/1971 | Lloyd et al. |
| 3,650,507 A | 3/1972 | Nyberg et al. |
| 3,680,562 A | 8/1972 | Wittes et al. |
| 3,683,929 A | 8/1972 | Holter |
| 3,742,952 A | 7/1973 | Magers et al. |
| 3,752,158 A | 8/1973 | Kariher |
| 3,768,476 A | 10/1973 | Raitto |
| 3,774,611 A | 12/1973 | Tussey et al. |
| 3,777,757 A | 12/1973 | Gray et al. |
| 3,783,870 A | 1/1974 | Schachet |
| 3,809,087 A | 5/1974 | Lewis |
| 3,820,546 A | 6/1974 | Chittenden et al. |
| 3,853,127 A | 12/1974 | Spademan |
| 3,875,941 A | 4/1975 | Adair |
| 3,920,023 A | 11/1975 | Dye et al. |
| 3,960,153 A | 6/1976 | Carey et al. |
| 3,982,546 A | 9/1976 | Friend |
| 4,022,209 A | 5/1977 | Nehring |
| 4,029,095 A | 6/1977 | Pena |
| 4,073,294 A | 2/1978 | Stanley et al. |
| 4,105,031 A | 8/1978 | Kurtz et al. |
| 4,112,949 A | 9/1978 | Rosenthal et al. |
| 4,116,366 A | 9/1978 | Takenakashima et al. |
| 4,120,715 A | 10/1978 | Ockwell et al. |
| 4,136,696 A | 1/1979 | Nehring |
| 4,143,853 A | 3/1979 | Abramson |
| 4,153,058 A | 5/1979 | Nehme |
| 4,170,300 A | 10/1979 | Pick |
| 4,174,053 A | 11/1979 | Shimizu |
| 4,187,848 A | 2/1980 | Taylor |
| 4,203,445 A | 5/1980 | Jessup et al. |
| 4,214,593 A | 7/1980 | Imbruce et al. |
| 4,257,629 A | 3/1981 | Maple et al. |
| 4,265,848 A | 5/1981 | Rusch et al. |
| 4,266,545 A | 5/1981 | Moss |
| 4,310,104 A | 1/1982 | Takatsuki |
| 4,315,513 A | 2/1982 | Nawash et al. |
| 4,334,551 A | 6/1982 | Pfister |
| 4,341,212 A | 7/1982 | Medwid |
| D267,433 S | 12/1982 | Pageau |
| 4,364,395 A | 12/1982 | Redmond et al. |
| D267,815 S | 2/1983 | Elliott et al. |
| 4,382,442 A | 5/1983 | Jones |
| 4,390,519 A | 6/1983 | Sawyer |
| 4,392,858 A | 7/1983 | George et al. |
| 4,393,873 A | 7/1983 | Nawash et al. |
| 4,396,382 A | 8/1983 | Goldhaber |
| 4,402,682 A | 9/1983 | Garver, Sr. et al. |
| 4,421,146 A | 12/1983 | Bond et al. |
| 4,427,425 A | 1/1984 | Briggs et al. |
| 4,429,693 A | 2/1984 | Blake et al. |
| 4,433,973 A | 2/1984 | Kurtz et al. |
| 4,439,190 A | 3/1984 | Protzmann et al. |
| 4,447,235 A | 5/1984 | Clarke |
| 4,455,141 A | 6/1984 | Todd |
| 4,464,168 A | 8/1984 | Redmond et al. |
| 4,475,904 A | 10/1984 | Wang |
| 4,476,866 A | 10/1984 | Chin |
| 4,479,495 A | 10/1984 | Isaacson |
| 4,479,818 A | 10/1984 | Briggs et al. |
| 4,490,003 A | 12/1984 | Robinson |
| 4,496,464 A | 1/1985 | Hensley |
| 4,501,363 A | 2/1985 | Isbey, Jr. |
| 4,511,163 A | 4/1985 | Harris et al. |
| 4,512,771 A | 4/1985 | Norton |
| 4,525,167 A | 6/1985 | Goldberg et al. |
| 4,539,985 A | 9/1985 | Magrath |
| 4,543,100 A | 9/1985 | Brodsky |
| 4,557,262 A | 12/1985 | Snow |
| 4,564,222 A | 1/1986 | Loker et al. |
| 4,569,674 A | 2/1986 | Phillips et al. |
| 4,583,972 A | 4/1986 | Hunter, III et al. |
| 4,605,400 A | 8/1986 | Kurtz et al. |
| 4,610,469 A | 9/1986 | Wolff-Mooij |
| 4,610,671 A | 9/1986 | Luther |
| 4,620,846 A | 11/1986 | Goldberg et al. |
| 4,642,088 A | 2/1987 | Gunter |
| 4,643,720 A | 2/1987 | Lanciano |
| 4,648,870 A | 3/1987 | Goldberg et al. |
| 4,666,433 A | 5/1987 | Parks |
| 4,669,463 A | 6/1987 | McConnell |
| 4,673,398 A | 6/1987 | Turner et al. |
| 4,675,020 A | 6/1987 | McPhee |
| 4,681,571 A | 7/1987 | Nehring |
| 4,685,901 A | 8/1987 | Parks |
| 4,685,908 A | 8/1987 | Kurtz |
| 4,701,163 A | 10/1987 | Parks |
| 4,702,733 A | 10/1987 | Wright et al. |
| 4,706,830 A | 11/1987 | Wareing |
| 4,738,671 A | 4/1988 | Elliott et al. |
| 4,740,202 A | 4/1988 | Stacey et al. |
| 4,741,678 A | 5/1988 | Nehring |
| 4,747,843 A | 5/1988 | Felix et al. |
| 4,747,844 A | 5/1988 | Elliott |
| 4,752,292 A | 6/1988 | Lopez et al. |
| 4,758,238 A | 7/1988 | Sundblom et al. |
| 4,781,674 A | 11/1988 | Redmond et al. |
| 4,790,567 A | 12/1988 | Kawano et al. |
| 4,809,679 A | 3/1989 | Shimonaka et al. |
| 4,813,929 A | 3/1989 | Semrad |
| 4,820,288 A | 4/1989 | Isono |
| 4,828,546 A | 5/1989 | McNeil et al. |

(56) References Cited

U.S. PATENT DOCUMENTS

| | | |
|---|---|---|
| 4,834,702 A | 5/1989 | Rocco |
| 4,834,802 A | 5/1989 | Prier |
| 4,844,087 A | 7/1989 | Garg |
| 4,850,955 A | 7/1989 | Newkirk |
| 4,857,042 A | 8/1989 | Schneider |
| 4,863,593 A | 9/1989 | Quick |
| 4,867,740 A | 9/1989 | East |
| 4,874,377 A | 10/1989 | Newgard et al. |
| 4,883,474 A | 11/1989 | Sheridan et al. |
| 4,883,476 A | 11/1989 | Kurtz et al. |
| 4,921,488 A | 5/1990 | Maitz et al. |
| 4,928,830 A | 5/1990 | Brewer |
| 4,929,235 A | 5/1990 | Merry et al. |
| 4,930,997 A | 6/1990 | Bennett |
| 4,936,837 A | 6/1990 | Wexler |
| 4,944,732 A | 7/1990 | Russo |
| 4,946,448 A | 8/1990 | Richmond |
| 4,946,449 A | 8/1990 | Davis, Jr. |
| 4,949,756 A | 8/1990 | Melinyshyn et al. |
| 4,950,256 A | 8/1990 | Luther et al. |
| 4,960,412 A | 10/1990 | Fink |
| 4,966,197 A | 10/1990 | Jaron et al. |
| 4,968,294 A | 11/1990 | Salama |
| 4,969,879 A | 11/1990 | Lichte |
| 4,969,890 A | 11/1990 | Sugita et al. |
| 4,973,311 A | 11/1990 | Iwakoshi et al. |
| 4,981,474 A | 1/1991 | Bopp et al. |
| 4,995,864 A | 2/1991 | Bartholomew et al. |
| 5,002,528 A | 3/1991 | Palestrant |
| 5,002,529 A | 3/1991 | Cunningham |
| 5,009,226 A | 4/1991 | Holt |
| 5,009,635 A | 4/1991 | Scarberry |
| 5,009,636 A | 4/1991 | Wortley et al. |
| 5,019,059 A | 5/1991 | Goldberg et al. |
| 5,019,096 A | 5/1991 | Fox, Jr. et al. |
| 5,024,653 A | 6/1991 | Kohnka |
| 5,037,403 A | 8/1991 | Garcia |
| 5,048,875 A | 9/1991 | Usui et al. |
| 5,052,998 A | 10/1991 | Zimmon |
| 5,053,014 A | 10/1991 | Van Heugten |
| 5,057,084 A | 10/1991 | Ensminger et al. |
| 5,060,833 A | 10/1991 | Edison et al. |
| 5,061,255 A | 10/1991 | Greenfeld et al. |
| 5,062,835 A | 11/1991 | Maitz et al. |
| 5,064,416 A | 11/1991 | Newgard et al. |
| 5,078,677 A | 1/1992 | Gentelia et al. |
| 5,078,689 A | 1/1992 | Keller |
| 5,078,699 A | 1/1992 | Haber et al. |
| 5,085,349 A | 2/1992 | Fawcett |
| 5,092,850 A | 3/1992 | Buma |
| 5,098,405 A | 3/1992 | Peterson et al. |
| 5,100,394 A | 3/1992 | Dudar et al. |
| 5,102,404 A | 4/1992 | Goldberg et al. |
| 5,106,054 A | 4/1992 | Mollenauer et al. |
| 5,112,323 A | 5/1992 | Winkler et al. |
| 5,123,677 A | 6/1992 | Kreczko et al. |
| 5,137,524 A | 8/1992 | Lynn et al. |
| 5,139,512 A | 8/1992 | Dreiling et al. |
| 5,141,499 A | 8/1992 | Zappacosta |
| 5,156,597 A | 10/1992 | Verreet et al. |
| 5,165,953 A | 11/1992 | Shlenker et al. |
| 5,188,622 A | 2/1993 | Muller et al. |
| 5,199,946 A | 4/1993 | Abramowitz |
| 5,207,655 A | 5/1993 | Sheridan |
| 5,215,538 A | 6/1993 | Larkin |
| 5,234,454 A | 8/1993 | Bangs |
| 5,238,217 A | 8/1993 | Fell |
| 5,242,422 A | 9/1993 | Schneberger et al. |
| 5,251,873 A | 10/1993 | Atkinson et al. |
| 5,261,897 A | 11/1993 | Kurtz et al. |
| 5,269,771 A | 12/1993 | Thomas et al. |
| 5,269,803 A | 12/1993 | Geary et al. |
| 5,279,551 A | 1/1994 | James |
| 5,279,601 A | 1/1994 | Lichte |
| 5,280,876 A | 1/1994 | Atkins |
| 5,295,657 A | 3/1994 | Atkinson |
| 5,295,658 A | 3/1994 | Atkinson et al. |
| 5,300,034 A | 4/1994 | Behnke et al. |
| 5,300,048 A | 4/1994 | Drewes, Jr. et al. |
| 5,304,121 A | 4/1994 | Sahatjian |
| 5,304,186 A | 4/1994 | Semler et al. |
| 5,304,201 A | 4/1994 | Rice |
| 5,309,924 A | 5/1994 | Peabody |
| 5,320,110 A | 6/1994 | Wang |
| 5,322,518 A | 6/1994 | Schneider et al. |
| 5,330,447 A | 7/1994 | Barth |
| 5,334,159 A | 8/1994 | Turkel |
| 5,334,166 A | 8/1994 | Palestrant |
| 5,344,401 A | 9/1994 | Radisch et al. |
| 5,345,929 A | 9/1994 | Jansson et al. |
| 5,352,198 A | 10/1994 | Goldenberg et al. |
| 5,356,391 A | 10/1994 | Stewart |
| 5,360,413 A | 11/1994 | Leason et al. |
| 5,390,898 A | 2/1995 | Smedley et al. |
| 5,399,165 A | 3/1995 | Paul, Jr. |
| 5,401,245 A | 3/1995 | Haining |
| 5,403,284 A | 4/1995 | Gross |
| 5,405,331 A | 4/1995 | Bahnke et al. |
| 5,407,434 A | 4/1995 | Gross |
| 5,423,334 A | 6/1995 | Jordan |
| 5,435,470 A | 7/1995 | Kim |
| 5,437,900 A | 8/1995 | Kuzowski |
| 5,456,675 A | 10/1995 | Wolbring et al. |
| 5,465,857 A | 11/1995 | Yang |
| 5,470,319 A | 11/1995 | Mayer |
| 5,472,325 A | 12/1995 | Svendsen |
| 5,472,435 A | 12/1995 | Sutton |
| 5,480,392 A | 1/1996 | Mous |
| 5,484,401 A | 1/1996 | Rodriguez |
| 5,489,269 A | 2/1996 | Aldrich et al. |
| 5,492,304 A | 2/1996 | Smith et al. |
| 5,496,299 A | 3/1996 | Felix et al. |
| 5,501,426 A | 3/1996 | Atkinson et al. |
| 5,505,717 A | 4/1996 | Moore |
| 5,507,733 A | 4/1996 | Larkin |
| 5,507,847 A | 4/1996 | George et al. |
| 5,509,433 A | 4/1996 | Paradis |
| 5,509,909 A | 4/1996 | Moy |
| 5,509,912 A | 4/1996 | Vaillancourt et al. |
| 5,514,117 A | 5/1996 | Lynn |
| 5,520,665 A | 5/1996 | Fleetwood et al. |
| 5,529,278 A | 6/1996 | Weldon |
| 5,535,785 A | 7/1996 | Werge et al. |
| 5,540,661 A | 7/1996 | Tomisaka et al. |
| 5,556,387 A | 9/1996 | Mollenauer et al. |
| 5,573,516 A | 11/1996 | Tyner |
| 5,576,072 A | 11/1996 | Hostettler et al. |
| 5,597,536 A | 1/1997 | Mayer |
| 5,613,491 A | 3/1997 | Kanner et al. |
| 5,628,735 A | 5/1997 | Skow |
| 5,628,908 A | 5/1997 | Kamen et al. |
| 5,636,875 A | 6/1997 | Wasser et al. |
| 5,637,103 A | 6/1997 | Kerwin et al. |
| 5,662,960 A | 9/1997 | Hostettler et al. |
| 5,674,192 A | 10/1997 | Sahatjian et al. |
| 5,676,346 A | 10/1997 | Leinsing |
| D385,889 S | 11/1997 | Kullas et al. |
| 5,685,866 A | 11/1997 | Lopez |
| 5,690,612 A | 11/1997 | Lopez et al. |
| 5,695,466 A | 12/1997 | Lopez et al. |
| 5,695,520 A | 12/1997 | Bruckner |
| 5,701,934 A | 12/1997 | Kuran et al. |
| 5,709,672 A | 1/1998 | Illner |
| 5,725,506 A | 3/1998 | Freeman et al. |
| 5,727,714 A | 3/1998 | Fawcett |
| 5,728,120 A | 3/1998 | Shani et al. |
| 5,733,496 A | 3/1998 | Avellanet |
| 5,735,826 A | 4/1998 | Richmond |
| 5,738,144 A | 4/1998 | Rogers |
| 5,738,656 A | 4/1998 | Wagner |
| 5,776,119 A | 7/1998 | Bilbo et al. |
| 5,779,657 A | 7/1998 | Daneshvar |
| 5,792,098 A | 8/1998 | Felix et al. |
| 5,792,108 A | 8/1998 | Felix et al. |

(56) References Cited

U.S. PATENT DOCUMENTS

| | | |
|---|---|---|
| 5,807,348 A | 9/1998 | Zinger et al. |
| 5,810,792 A | 9/1998 | Fangrow, Jr. et al. |
| 5,814,024 A | 9/1998 | Thompson et al. |
| 5,823,961 A | 10/1998 | Fields et al. |
| 5,830,185 A | 11/1998 | Block, Jr. |
| 5,839,715 A | 11/1998 | Leinsing |
| 5,873,853 A | 2/1999 | Keilman et al. |
| 5,897,782 A | 4/1999 | Chatelin et al. |
| 5,904,334 A | 5/1999 | Grunert et al. |
| 5,921,972 A | 7/1999 | Skow |
| 5,937,885 A | 8/1999 | Sampson |
| 5,938,176 A | 8/1999 | Falconer |
| 5,944,703 A | 8/1999 | Dixon et al. |
| 5,947,953 A | 9/1999 | Ash et al. |
| 5,954,313 A | 9/1999 | Ryan |
| 5,954,706 A | 9/1999 | Sahatjian |
| 5,957,898 A | 9/1999 | Jepson et al. |
| 5,957,912 A | 9/1999 | Heitzmann |
| 5,961,497 A | 10/1999 | Larkin |
| 5,971,357 A | 10/1999 | Denton et al. |
| 5,972,441 A | 10/1999 | Campbell et al. |
| 5,976,650 A | 11/1999 | Campbell et al. |
| 5,984,891 A | 11/1999 | Keilman et al. |
| 5,997,486 A | 12/1999 | Burek et al. |
| 5,997,564 A | 12/1999 | Shehata et al. |
| 6,001,079 A | 12/1999 | Pourchez |
| 6,024,731 A | 2/2000 | Seddon et al. |
| 6,025,044 A | 2/2000 | Campbell et al. |
| 6,027,779 A | 2/2000 | Campbell et al. |
| 6,027,811 A | 2/2000 | Campbell et al. |
| 6,029,946 A | 2/2000 | Doyle |
| 6,039,302 A | 3/2000 | Cote, Sr. et al. |
| 6,039,714 A | 3/2000 | Cracauer et al. |
| 6,056,730 A | 5/2000 | Greter |
| 6,056,731 A | 5/2000 | Koetke et al. |
| 6,063,062 A | 5/2000 | Paradis |
| 6,068,011 A | 5/2000 | Paradis |
| 6,068,646 A | 5/2000 | Lam |
| 6,070,767 A | 6/2000 | Gardner et al. |
| 6,079,444 A | 6/2000 | Harris et al. |
| 6,089,541 A | 7/2000 | Weinheimer et al. |
| 6,093,154 A | 7/2000 | Burek et al. |
| 6,103,695 A | 8/2000 | Lane et al. |
| 6,106,502 A | 8/2000 | Richmond |
| 6,106,503 A | 8/2000 | Pfeiderer et al. |
| 6,113,068 A | 9/2000 | Ryan |
| 6,117,114 A | 9/2000 | Paradis |
| 6,120,264 A | 9/2000 | Wang |
| 6,129,699 A | 10/2000 | Haight et al. |
| 6,129,750 A | 10/2000 | Tockman et al. |
| 6,132,403 A | 10/2000 | Lopez |
| 6,132,407 A | 10/2000 | Genese et al. |
| 6,149,129 A | 11/2000 | Harris et al. |
| 6,156,004 A | 12/2000 | Tremaine et al. |
| 6,165,217 A | 12/2000 | Hayes |
| 6,168,137 B1 | 1/2001 | Paradis |
| 6,170,800 B1 | 1/2001 | Meloul et al. |
| 6,171,287 B1 | 1/2001 | Lynn et al. |
| 6,193,682 B1 | 2/2001 | Ahmed |
| 6,196,992 B1 | 3/2001 | Keilman et al. |
| 6,200,292 B1 | 3/2001 | French et al. |
| 6,217,556 B1 | 4/2001 | Ellingson et al. |
| 6,221,425 B1 | 4/2001 | Michal et al. |
| 6,231,507 B1 | 5/2001 | Zikorus et al. |
| 6,234,992 B1 | 5/2001 | Haight et al. |
| 6,234,996 B1 | 5/2001 | Bagaoisan et al. |
| 6,235,009 B1 | 5/2001 | Skow |
| 6,245,048 B1 | 6/2001 | Fangrow, Jr. et al. |
| 6,254,061 B1 | 7/2001 | Levine et al. |
| 6,254,581 B1 | 7/2001 | Scott |
| 6,261,276 B1 | 7/2001 | Reitsma |
| 6,261,282 B1 | 7/2001 | Jepson et al. |
| 6,283,949 B1 | 9/2001 | Roorda |
| 6,287,285 B1 | 9/2001 | Michal et al. |
| 6,293,929 B1 | 9/2001 | Smith et al. |
| 6,299,131 B1 | 10/2001 | Ryan |
| 6,299,593 B1 | 10/2001 | Wakabayashi |
| 6,309,423 B2 | 10/2001 | Hayes |
| 6,319,235 B1 | 11/2001 | Yoshimo |
| 6,328,765 B1 | 12/2001 | Hardwick et al. |
| 6,332,892 B1 | 12/2001 | Desmond, III et al. |
| 6,344,033 B1 | 2/2002 | Jepson et al. |
| 6,352,525 B1 | 3/2002 | Wakabayashi |
| 6,375,024 B1 | 4/2002 | Park |
| 6,391,009 B1 | 5/2002 | Crosa Dorado |
| 6,409,716 B1 | 6/2002 | Sahatiian et al. |
| 6,428,520 B1 | 8/2002 | Lopez et al. |
| 6,447,473 B1 | 9/2002 | Levine et al. |
| 6,468,190 B1 | 10/2002 | Fazio et al. |
| 6,482,190 B1 | 11/2002 | Genese et al. |
| 6,491,668 B1 | 12/2002 | Paradis |
| 6,500,164 B1 | 12/2002 | Turner et al. |
| 6,530,951 B1 | 3/2003 | Bates et al. |
| 6,541,116 B2 | 4/2003 | Michal et al. |
| 6,551,267 B1 | 4/2003 | Cohen et al. |
| 6,554,808 B1 | 4/2003 | Cook |
| 6,562,013 B1 | 5/2003 | Marasco, Jr. |
| RE38,145 E | 6/2003 | Lynn |
| 6,620,132 B1 | 9/2003 | Skow |
| 6,626,418 B2 | 9/2003 | Kiehne et al. |
| 6,629,707 B1 | 10/2003 | Yamaguchi et al. |
| 6,634,384 B2 | 10/2003 | Skeens et al. |
| 6,635,020 B2 | 10/2003 | Tripp, Jr. et al. |
| 6,637,726 B1 | 10/2003 | Yamamoto |
| 6,641,562 B1 | 11/2003 | Peterson |
| 6,641,574 B2 | 11/2003 | Badia Segura et al. |
| 6,645,547 B1 | 11/2003 | Shekalim et al. |
| 6,647,986 B1 | 11/2003 | Korotko et al. |
| 6,651,956 B2 | 11/2003 | Miller |
| 6,652,484 B1 | 11/2003 | Hunckler et al. |
| 6,655,655 B1 | 12/2003 | Matkovich et al. |
| 6,656,517 B2 | 12/2003 | Michal et al. |
| 6,665,888 B1 | 12/2003 | Kwak |
| 6,669,681 B2 | 12/2003 | Jepson et al. |
| 6,673,049 B2 | 1/2004 | Hommann et al. |
| 6,673,051 B2 | 1/2004 | Flinchbaugh |
| 6,695,817 B1 | 2/2004 | Fangrow, Jr. |
| 6,699,213 B1 | 3/2004 | Annis et al. |
| 6,706,022 B1 | 3/2004 | Leinsing et al. |
| 6,708,950 B2 | 3/2004 | Christensen et al. |
| 6,719,991 B2 | 4/2004 | Darouiche et al. |
| 6,726,672 B1 | 4/2004 | Hanly et al. |
| 6,730,107 B2 | 5/2004 | Kelley et al. |
| 6,733,000 B2 | 5/2004 | McCarty et al. |
| 6,733,481 B2 | 5/2004 | Ow |
| 6,745,998 B2 | 6/2004 | Doyle |
| 6,755,391 B2 | 6/2004 | Newton et al. |
| 6,780,497 B1 | 8/2004 | Walter |
| 6,802,836 B2 | 10/2004 | Bouphavichith et al. |
| 6,808,161 B1 | 10/2004 | Hishikawa |
| D500,132 S | 12/2004 | Peterson et al. |
| D500,133 S | 12/2004 | Peterson et al. |
| 6,833,001 B2 | 12/2004 | Chao |
| D500,552 S | 1/2005 | Peterson et al. |
| D500,853 S | 1/2005 | Peterson et al. |
| 6,840,501 B2 | 1/2005 | Doyle |
| 6,849,061 B2 | 2/2005 | Wagner |
| 6,896,665 B2 | 5/2005 | Picha et al. |
| 6,897,349 B2 | 5/2005 | Gibbins et al. |
| 6,916,379 B2 | 7/2005 | Shekalim et al. |
| 6,936,031 B2 | 8/2005 | Caleffi |
| 6,972,001 B2 | 12/2005 | Emig et al. |
| 6,994,315 B2 | 2/2006 | Ryan et al. |
| 7,004,923 B2 | 2/2006 | Deniega et al. |
| 7,004,934 B2 | 2/2006 | Vaillancourt |
| 7,008,407 B1 | 3/2006 | Kamp |
| 7,044,441 B2 | 5/2006 | Doyle |
| 7,048,724 B2 | 5/2006 | Grossman et al. |
| 7,048,962 B2 | 5/2006 | Shekalim et al. |
| 7,052,603 B2 | 5/2006 | Schick |
| 7,090,191 B2 | 8/2006 | Matkovich et al. |
| 7,094,218 B2 | 8/2006 | Rome et al. |
| 7,100,890 B2 | 9/2006 | Cote, Sr. et al. |
| 7,101,353 B2 | 9/2006 | Lui et al. |

(56) References Cited

U.S. PATENT DOCUMENTS

| | | |
|---|---|---|
| 7,112,177 B2 | 9/2006 | Christensen et al. |
| 7,150,740 B2 | 12/2006 | Bennett et al. |
| 7,163,495 B2 | 1/2007 | Fazio et al. |
| 7,165,568 B2 | 1/2007 | Kessell et al. |
| 7,179,244 B2 | 2/2007 | Smith et al. |
| 7,184,825 B2 | 2/2007 | Leinsing et al. |
| 7,207,946 B2 | 4/2007 | Sirokman |
| 7,303,553 B2 | 12/2007 | Ott |
| 7,311,690 B2 | 12/2007 | Burnett |
| 7,314,061 B2 | 1/2008 | Peppel |
| 7,320,674 B2 | 1/2008 | Ruddell et al. |
| 7,341,240 B2 | 3/2008 | Ciesielka |
| 7,377,915 B2 | 5/2008 | Rasmussen et al. |
| 7,383,073 B1 | 6/2008 | Abovitz et al. |
| 7,396,348 B2 | 7/2008 | Newton et al. |
| 7,401,703 B2 | 7/2008 | McMichael et al. |
| 7,452,346 B2 | 11/2008 | Axelsson |
| 7,452,354 B2 | 11/2008 | Bright et al. |
| 7,468,058 B2 | 12/2008 | Kanie et al. |
| 7,497,848 B2 | 3/2009 | Leinsing et al. |
| 7,497,849 B2 | 3/2009 | Fangrow, Jr. |
| 7,524,311 B2 | 4/2009 | Phung et al. |
| 7,530,546 B2 | 5/2009 | Ryan et al. |
| 7,547,302 B2 | 6/2009 | Porto et al. |
| 7,563,243 B2 | 7/2009 | Mendels |
| 7,569,045 B2 | 8/2009 | Deniega et al. |
| 7,578,803 B2 | 8/2009 | Rome et al. |
| 7,584,767 B2 | 9/2009 | Funamura et al. |
| 7,591,805 B2 | 9/2009 | Lampropoulos |
| 7,594,910 B2 | 9/2009 | Butts et al. |
| 7,611,503 B2 | 11/2009 | Spohn et al. |
| 7,614,123 B2 | 11/2009 | Schweikert |
| 7,621,903 B2 | 11/2009 | DeLegge |
| 7,628,774 B2 | 12/2009 | Fangrow, Jr. |
| 7,628,779 B2 | 12/2009 | Aneas |
| 7,632,260 B2 | 12/2009 | Antoine |
| 7,637,893 B2 | 12/2009 | Christensen et al. |
| 7,644,722 B2 | 1/2010 | Christensen et al. |
| 7,674,248 B2 | 3/2010 | Anderson et al. |
| 7,678,092 B2 | 3/2010 | Matloub et al. |
| 7,682,332 B2 | 3/2010 | Tanaka |
| 7,691,090 B2 | 4/2010 | Belley et al. |
| 7,695,458 B2 | 4/2010 | Belley et al. |
| 7,708,027 B2 | 5/2010 | Yokota et al. |
| 7,717,891 B1 | 5/2010 | Whaley |
| 7,726,315 B2 | 6/2010 | Field |
| 7,726,328 B2 | 6/2010 | Christensen et al. |
| 7,736,336 B2 | 6/2010 | Plilshka et al. |
| 7,744,594 B2 | 6/2010 | Yamazaki et al. |
| 7,758,574 B2 | 7/2010 | Hijii et al. |
| 7,766,304 B2 | 8/2010 | Phillips |
| 7,766,938 B2 | 8/2010 | McGurk et al. |
| 7,780,612 B2 | 8/2010 | Ross |
| 7,798,974 B2 | 9/2010 | Sirokman |
| 7,815,168 B2 | 10/2010 | Vangsness et al. |
| 7,824,384 B2 | 11/2010 | Watson, Jr. |
| 7,833,194 B2 | 11/2010 | Owens et al. |
| 7,854,731 B2 | 12/2010 | Rome et al. |
| 7,857,284 B2 | 12/2010 | Kimball et al. |
| 7,867,204 B2 | 1/2011 | Bartholomew et al. |
| 7,879,012 B2 | 2/2011 | Kane et al. |
| 7,892,181 B2 | 2/2011 | Christensen et al. |
| 8,007,257 B2 | 8/2011 | Heaton et al. |
| 8,048,046 B2 | 11/2011 | Hudspeth et al. |
| 8,048,056 B2 | 11/2011 | Picha et al. |
| 8,052,671 B2 | 11/2011 | Christensen et al. |
| 8,057,448 B2 | 11/2011 | Williams et al. |
| 8,074,848 B2 | 12/2011 | Pittl et al. |
| 8,083,332 B2 | 12/2011 | Price et al. |
| 8,147,417 B2 | 4/2012 | Gavriely |
| 8,177,772 B2 | 5/2012 | Christensen et al. |
| 8,210,166 B2 | 7/2012 | Denton et al. |
| 8,224,422 B2 | 7/2012 | Mottola et al. |
| 8,235,971 B2 | 8/2012 | Christensen et al. |
| 8,246,590 B2 | 8/2012 | Hu et al. |
| 8,337,475 B2 | 12/2012 | Christensen et al. |
| 8,435,221 B2 | 5/2013 | Hu et al. |
| 8,632,840 B2 | 1/2014 | Avitable |
| 8,636,721 B2 | 1/2014 | Alam et al. |
| 8,814,839 B2 | 8/2014 | Christensen et al. |
| 8,845,680 B2 | 9/2014 | Lampropoulos et al. |
| 9,295,764 B2 | 3/2016 | Christensen et al. |
| 9,332,994 B2 | 5/2016 | Pancholy et al. |
| 9,393,353 B2 | 7/2016 | Alam et al. |
| D804,663 S | 12/2017 | Jenkins |
| D821,590 S | 6/2018 | Hylton et al. |
| 10,172,625 B2 | 1/2019 | Wada et al. |
| 10,463,833 B2 | 11/2019 | Clarke et al. |
| 10,492,797 B2 | 12/2019 | Okamura |
| D893,034 S | 8/2020 | Kase et al. |
| 2001/0047158 A1 | 11/2001 | Ladd |
| 2002/0002351 A1 | 1/2002 | Cote et al. |
| 2002/0123715 A1 | 9/2002 | Sorenson et al. |
| 2002/0148467 A1 | 10/2002 | Bosse et al. |
| 2002/0153503 A1 | 10/2002 | Newton et al. |
| 2002/0188315 A1 | 12/2002 | Guzman et al. |
| 2002/0198458 A1 | 12/2002 | Tripp et al. |
| 2003/0017920 A1 | 1/2003 | Fazio et al. |
| 2003/0032940 A1 | 2/2003 | Doyle |
| 2003/0040769 A1 | 2/2003 | Kelley et al. |
| 2003/0055453 A1 | 3/2003 | Akerfeldt |
| 2003/0062498 A1 | 4/2003 | Decler et al. |
| 2003/0111121 A1 | 6/2003 | Skeens et al. |
| 2003/0139766 A1 | 7/2003 | McEwen et al. |
| 2003/0149359 A1 | 8/2003 | Smith |
| 2003/0159755 A1 | 8/2003 | Wessberg |
| 2003/0165647 A1 | 9/2003 | Kaneko et al. |
| 2003/0173536 A1 | 9/2003 | Christensen et al. |
| 2004/0049157 A1 | 3/2004 | Plishka et al. |
| 2004/0078026 A1 | 4/2004 | Wagner |
| 2004/0082923 A1 | 4/2004 | Field |
| 2004/0116894 A1 | 6/2004 | DeLegge |
| 2004/0215155 A1 | 10/2004 | Wolfe et al. |
| 2004/0232696 A1 | 11/2004 | Andre |
| 2004/0267163 A1 | 12/2004 | Opie et al. |
| 2005/0025816 A1 | 2/2005 | Tanaka |
| 2005/0090805 A1 | 4/2005 | Shaw et al. |
| 2005/0113866 A1 | 5/2005 | Heinz et al. |
| 2005/0121638 A1 | 6/2005 | Doyle |
| 2005/0125025 A1 | 6/2005 | Rioux |
| 2005/0131357 A1 | 6/2005 | Denton et al. |
| 2005/0143691 A1 | 6/2005 | Picha et al. |
| 2005/0203463 A1 | 9/2005 | Lampropoulos |
| 2005/0203597 A1 | 9/2005 | Yamazaki et al. |
| 2005/0209572 A1 | 9/2005 | Rome et al. |
| 2005/0209581 A1 | 9/2005 | Butts et al. |
| 2005/0251102 A1 | 11/2005 | Hegland et al. |
| 2005/0261636 A1 | 11/2005 | Rome et al. |
| 2005/0261664 A1 | 11/2005 | Rome et al. |
| 2005/0267445 A1 | 12/2005 | Mendels |
| 2005/0267487 A1 | 12/2005 | Christensen et al. |
| 2005/0281822 A1 | 12/2005 | Cedarbaum et al. |
| 2006/0009801 A1 | 1/2006 | McGurk et al. |
| 2006/0015086 A1 | 1/2006 | Rasmussen et al. |
| 2006/0058702 A1 | 3/2006 | Christensen et al. |
| 2006/0058841 A1 | 3/2006 | Mills et al. |
| 2006/0079853 A1 | 4/2006 | Christensen et al. |
| 2006/0116721 A1 | 6/2006 | Yun et al. |
| 2006/0118749 A1 | 6/2006 | Ryan et al. |
| 2006/0129109 A1 | 6/2006 | Shaw et al. |
| 2006/0190026 A1 | 8/2006 | Sanders |
| 2006/0200089 A1 | 9/2006 | Lopez et al. |
| 2006/0211998 A1 | 9/2006 | Fangrow |
| 2006/0211999 A1 | 9/2006 | Fangrow |
| 2006/0212000 A1 | 9/2006 | Fangrow |
| 2006/0212001 A1 | 9/2006 | Fangrow |
| 2006/0212002 A1 | 9/2006 | Fangrow |
| 2006/0212003 A1 | 9/2006 | Fangrow |
| 2006/0264842 A1 | 11/2006 | Fangrow |
| 2007/0038143 A1 | 2/2007 | Christensen et al. |
| 2007/0073270 A1 | 3/2007 | Christensen et al. |
| 2007/0083157 A1 | 4/2007 | Belley et al. |
| 2007/0083162 A1 | 4/2007 | O'Reagan et al. |
| 2007/0100295 A1 | 5/2007 | Belley et al. |

(56) References Cited

U.S. PATENT DOCUMENTS

| | | |
|---|---|---|
| 2007/0100322 A1 | 5/2007 | Venugopalan et al. |
| 2007/0100324 A1 | 5/2007 | Tempel et al. |
| 2007/0235674 A1 | 10/2007 | Vangsness et al. |
| 2007/0235675 A1 | 10/2007 | Kimball et al. |
| 2007/0235676 A1 | 10/2007 | Vangsness et al. |
| 2007/0239092 A1 | 10/2007 | Ross |
| 2007/0248810 A1 | 10/2007 | McGee et al. |
| 2007/0255167 A1 | 11/2007 | Christensen et al. |
| 2007/0255229 A1 | 11/2007 | Kane et al. |
| 2007/0260195 A1 | 11/2007 | Bartholomew et al. |
| 2007/0270720 A1 | 11/2007 | Fry |
| 2007/0270764 A1 | 11/2007 | Gordon |
| 2007/0282268 A1 | 12/2007 | Mayse |
| 2008/0097407 A1 | 2/2008 | Plishka |
| 2008/0091174 A1 | 4/2008 | Alam et al. |
| 2008/0103408 A1 | 5/2008 | Denton et al. |
| 2008/0114316 A1 | 5/2008 | Christensen et al. |
| 2008/0177175 A1 | 7/2008 | Mottola et al. |
| 2008/0277610 A1 | 11/2008 | Bahner et al. |
| 2009/0012493 A1 | 1/2009 | Harig |
| 2009/0043270 A1 | 2/2009 | Noyce et al. |
| 2009/0069763 A1 | 3/2009 | DiCarlo et al. |
| 2009/0142741 A1 | 6/2009 | Ault et al. |
| 2009/0209896 A1 | 8/2009 | Selevan |
| 2009/0219353 A1 | 9/2009 | Price et al. |
| 2009/0240182 A1 | 9/2009 | Weber et al. |
| 2009/0261130 A1 | 10/2009 | Pittl et al. |
| 2009/0281565 A1 | 11/2009 | McNeese |
| 2009/0312725 A1 | 12/2009 | Braga |
| 2009/0314973 A1 | 12/2009 | Christensen et al. |
| 2010/0030163 A1 | 2/2010 | Carrez et al. |
| 2010/0044609 A1 | 2/2010 | Matsubara |
| 2010/0211000 A1 | 8/2010 | Killion et al. |
| 2010/0217202 A1 | 8/2010 | Clark |
| 2010/0274229 A1 | 10/2010 | Duocastella Codina et al. |
| 2010/0280541 A1 | 11/2010 | Lampropoulos |
| 2011/0009849 A1 | 1/2011 | Christensen et al. |
| 2011/0022012 A1 | 1/2011 | Kerr et al. |
| 2011/0071415 A1 | 3/2011 | Karwoski et al. |
| 2011/0083665 A1 | 4/2011 | Denton et al. |
| 2011/0105963 A1 | 5/2011 | Hu et al. |
| 2011/0172510 A1 | 7/2011 | Chickering, III |
| 2011/0238022 A1 | 9/2011 | Massi et al. |
| 2011/0275964 A1 | 11/2011 | Greener |
| 2011/0276017 A1 | 11/2011 | Schuessler et al. |
| 2012/0220984 A1 | 8/2012 | Christensen et al. |
| 2012/0221041 A1 | 8/2012 | Hansson et al. |
| 2012/0238934 A1 | 9/2012 | During |
| 2012/0296369 A1 | 11/2012 | Atthoff et al. |
| 2013/0023734 A1 | 1/2013 | Okamura |
| 2013/0079723 A1 | 3/2013 | Andino et al. |
| 2013/0090614 A1 | 4/2013 | Christensen et al. |
| 2013/0165787 A1 | 6/2013 | Ukawa et al. |
| 2013/0237866 A1* | 9/2013 | Cohen .................. A61B 5/445 600/502 |
| 2013/0245675 A1 | 9/2013 | Wada et al. |
| 2013/0289613 A1 | 10/2013 | Wada et al. |
| 2014/0012120 A1 | 1/2014 | Cohen et al. |
| 2014/0012313 A1 | 1/2014 | Finkielsztien et al. |
| 2014/0125718 A1 | 5/2014 | Morrison et al. |
| 2014/0142615 A1 | 5/2014 | Corrigan, Jr. |
| 2014/0182594 A1 | 7/2014 | Alam et al. |
| 2014/0236221 A1 | 8/2014 | Zhadkevich |
| 2014/0288408 A1 | 9/2014 | Deutsch |
| 2014/0358095 A1 | 12/2014 | Christensen et al. |
| 2015/0018868 A1 | 1/2015 | Pancholy |
| 2015/0018869 A1 | 1/2015 | Benz et al. |
| 2015/0032149 A1* | 1/2015 | Croushorn ........... A61B 17/135 606/202 |
| 2015/0164436 A1 | 6/2015 | Maron et al. |
| 2015/0201948 A1 | 7/2015 | Kornowski et al. |
| 2015/0314074 A1 | 11/2015 | Howlett et al. |
| 2015/0327870 A1 | 11/2015 | Fortson et al. |
| 2015/0327871 A1* | 11/2015 | Fortson ................ A61B 17/135 606/202 |
| 2015/0342615 A1 | 12/2015 | Keinan et al. |
| 2016/0058988 A1 | 3/2016 | Kesten et al. |
| 2016/0102269 A1 | 4/2016 | Benz |
| 2016/0183951 A1 | 6/2016 | Pancholy |
| 2016/0279395 A1 | 9/2016 | Lampropoulos et al. |
| 2017/0000988 A1 | 1/2017 | Stevens et al. |
| 2017/0007807 A1 | 1/2017 | Weerakoon et al. |
| 2017/0273693 A1 | 9/2017 | Morrison et al. |
| 2018/0000494 A1 | 1/2018 | Wada et al. |
| 2018/0008281 A1 | 1/2018 | Hazama |
| 2018/0008282 A1 | 1/2018 | Hazama et al. |
| 2018/0008283 A1 | 1/2018 | Hazama |
| 2018/0014832 A1 | 1/2018 | Lampropoulos et al. |
| 2018/0028195 A1 | 2/2018 | Benz et al. |
| 2018/0042615 A1 | 2/2018 | Kimura et al. |
| 2018/0070956 A1 | 3/2018 | Lampropoulos et al. |
| 2018/0185032 A1 | 7/2018 | Matsushita et al. |
| 2018/0250017 A1 | 9/2018 | Matsushita et al. |
| 2018/0280008 A1 | 10/2018 | Okamura |
| 2019/0021742 A1 | 1/2019 | Hazama |
| 2019/0029693 A1 | 1/2019 | Okamura |
| 2019/0046214 A1 | 2/2019 | Hazama |
| 2019/0090886 A1 | 3/2019 | Brown et al. |
| 2019/0133602 A1 | 5/2019 | Kiemeneij et al. |
| 2019/0133604 A1 | 5/2019 | Maeda et al. |
| 2019/0133605 A1 | 5/2019 | Hazama et al. |
| 2019/0133606 A1 | 5/2019 | Hazama |
| 2019/0133607 A1 | 5/2019 | Hazama |
| 2019/0150938 A1 | 5/2019 | Hazama et al. |
| 2019/0167273 A1 | 6/2019 | Morrison et al. |
| 2019/0274692 A1 | 9/2019 | Lampropoulos et al. |
| 2019/0314035 A1 | 10/2019 | Hopkinson et al. |
| 2020/0029946 A1 | 1/2020 | Green et al. |

FOREIGN PATENT DOCUMENTS

| | | |
|---|---|---|
| CN | 201861701 | 6/2011 |
| CN | 208864401 | 5/2019 |
| CN | 209695299 | 11/2019 |
| DE | 1616493 | 6/1971 |
| DE | 4006696 | 11/1990 |
| DE | 9105229 | 6/1991 |
| DE | 4311715 | 10/1994 |
| EP | 0270205 | 6/1988 |
| EP | 0829248 | 3/1998 |
| EP | 1547537 | 6/2005 |
| EP | 1684824 | 8/2006 |
| EP | 1740253 | 1/2007 |
| EP | 1782850 | 5/2007 |
| FR | 2551978 | 3/1985 |
| FR | 2828231 | 2/2003 |
| GB | 2109239 | 6/1983 |
| GB | 2394761 | 5/2004 |
| JP | 2002049660 | 2/1990 |
| JP | 2005115556 | 5/1993 |
| JP | H6504468 | 5/1994 |
| JP | H666642 | 9/1994 |
| JP | 2000517216 | 12/2000 |
| JP | 2002177379 | 6/2002 |
| JP | 2012010823 | 1/2012 |
| JP | 2013111444 | 6/2013 |
| JP | 6211285 | 10/2014 |
| JP | 2014200308 | 10/2014 |
| JP | 6261368 | 8/2015 |
| JP | 2015150298 | 8/2015 |
| JP | 6389510 | 9/2015 |
| JP | 6261420 | 11/2015 |
| JP | 2015188608 | 11/2015 |
| JP | 2017000259 | 1/2017 |
| JP | 2017000260 | 1/2017 |
| JP | 2017047036 | 3/2017 |
| JP | 2018011798 | 1/2018 |
| JP | 2018011867 | 1/2018 |
| JP | 2018019927 | 2/2018 |
| JP | 2018033602 | 3/2018 |
| JP | 2018075257 | 5/2018 |
| JP | 2018171081 | 11/2018 |
| JP | 2019047956 | 3/2019 |
| JP | 2019058498 | 4/2019 |

(56) References Cited

FOREIGN PATENT DOCUMENTS

| | | |
|---|---|---|
| JP | 6544854 | 6/2019 |
| JP | 6559128 | 7/2019 |
| JP | 2019154915 | 9/2019 |
| JP | 2019166265 | 10/2019 |
| JP | 2019208953 | 12/2019 |
| JP | 2019216947 | 12/2019 |
| JP | 2019217130 | 12/2019 |
| JP | 2020014588 | 1/2020 |
| JP | 6667234 | 2/2020 |
| JP | 2020018686 | 2/2020 |
| JP | 2020022679 | 2/2020 |
| JP | 2020039815 | 3/2020 |
| JP | 2020039816 | 3/2020 |
| WO | 1990003194 | 4/1990 |
| WO | 1992007591 | 5/1992 |
| WO | 1995001135 | 1/1995 |
| WO | 199855072 | 12/1998 |
| WO | 200204065 | 1/2002 |
| WO | 2003001993 | 1/2003 |
| WO | 2003018105 | 3/2003 |
| WO | 2004041313 | 5/2004 |
| WO | 2005007213 | 1/2005 |
| WO | 2005044716 | 5/2005 |
| WO | 2005052366 | 6/2005 |
| WO | 2005099805 | 10/2005 |
| WO | 2005107843 | 11/2005 |
| WO | 2006004943 | 1/2006 |
| WO | 2006055288 | 5/2006 |
| WO | 2006060248 | 6/2006 |
| WO | 2006066023 | 6/2006 |
| WO | 2007038643 | 4/2007 |
| WO | 2007116386 | 10/2007 |
| WO | 2008115439 | 9/2008 |
| WO | 2008142580 | 11/2008 |
| WO | 2009027665 | 3/2009 |
| WO | 2009081180 | 7/2009 |
| WO | 2009118521 | 10/2009 |
| WO | 2010028044 | 3/2010 |
| WO | 2010091356 | 8/2010 |
| WO | 2011107972 | 9/2011 |
| WO | 2015141786 | 9/2015 |
| WO | 2016118695 | 7/2016 |
| WO | 2017043536 | 3/2017 |
| WO | 2018017365 | 1/2018 |

OTHER PUBLICATIONS

European Search Report dated Feb. 27, 2020 for EP17851579.7.
European Search Report dated Sep. 7, 2017 for EP 09763115.4.
International Search Report and Written Opinion dated Apr. 2, 2019 for PCT/US2018/060089.
International Search Report and Written Opinion dated May 14, 2019 for PCT/US2018/058992.
International Search Report and Written Opinion dated Jun. 12, 2019 for PCT/US2019/020980.
International Search Report and Written Opinion dated Jul. 30, 2019 for PCT/US2019/026785.
International Search Report and Written Opinion dated Nov. 28, 2017 for PCT/US2017/041726.
International Search Report and Written Opinion dated Dec. 26, 2017 for PCT/US2017/051715.
International Search Report dated Nov. 18, 2009 for PCT/US2009/042868.
MedPlus, Inc., Tourniquet (Radial Artery Compression Device), http://www.bikudo.com/product_search/details/187473/tourniquet_radial_artey_compression_device.html Nov. 24, 2009.
Notice of Allowance dated Jun. 9, 2014 for U.S. Appl. No. 13/741,046.
Notice of Allowance dated Oct. 16, 2012 for U.S. Appl. No. 12/435,227.
Office Action dated Jan. 8, 2020 for U.S. Appl. No. 15/648,110.
Office Action dated Jan. 10, 2019 for U.S. Appl. No. 15/705,759.
Office Action dated Feb. 14, 2014 for U.S. Appl. No. 13/741,046.
Office Action dated Mar. 2, 2011 for U.S. Appl. No. 12/349,405.
Office Action dated Mar. 5, 2013 for U.S. Appl. No. 13/741,046.
Office Action dated May 28, 2019 for U.S. Appl. No. 15/648,110.
Office Action dated Jun. 6, 2016 for U.S. Appl. No. 14/033,177.
European Search Report dated Jul. 9, 2021 for EP18876110.0.
Office Action dated May 25, 2021 for U.S. Appl. No. 16/380,505.
Office Action dated Jul. 23, 2021 for U.S. Appl. No. 16/179,257.
Office Action dated Feb. 16, 2021 for U.S. Appl. No. 16/380,505.
Office Action dated Apr. 12, 2021 for U.S. Appl. No. 16/179,257.
Office Action dated Jun. 28, 2011 for U.S. Appl. No. 12/349,405.
Office Action dated Aug. 17, 2012 for U.S. Appl. No. 12/349,405.
Office Action dated Sep. 6, 2019 for U.S. Appl. No. 15/705,759.
Office Action dated Sep. 16, 2020 for U.S. Appl. No. 16/380,505.
Office Action dated Oct. 8, 2020 for U.S. Appl. No. 16/179,257.
Office Action dated Nov. 3, 2015 for U.S. Appl. No. 14/033,177.
Office Action dated Dec. 8, 2011 for U.S. Appl. No. 12/349,405.
Office Action dated Dec. 27, 2016 for U.S. Appl. No. 14/033,177.
Merit Medical Adds 2 New Products for Assisting Hemostasis, Posted at Merit.com, no posting date, retrieved Aug. 26, 2020 online https://www.merit.com/articles/merit-medical-adds-2-new-products-assisting-hemostasis (2020).
Pua, et al., "Snuffbox" Distal Radial Access, J Vasc Interv Radiol, No. 29:44 ,2018.
Zhou, et al., Transient Ulnar Artery Compression Facilitates Transradial Access, Medicine, No. 95:48 ,2016.
European Search Report dated Apr. 23, 2021 for EP18872642.6.
European Search Report dated Nov. 23, 2021 for EP19784978.9.
European Supplemental Search Report dated Aug. 17, 2012 for EP04811627.1.
Extended European Search Report dated Oct. 28, 2021 for EP19763606.1.
International Search Report and Written Opinion dated Jan. 5, 2007 for PCT/US2006/037766.
International Search Report and Written Opinion dated Jan. 25, 2007 for PCT/US2006/037766.
International Search Report and Written Opinion dated Jul. 5, 2005 for PCT/US2004/38937.
Notice of Allowance dated Jan. 12, 2010 for U.S. Appl. No. 11/248,082.
Notice of Allowance dated Apr. 12, 2010 for U.S. Appl. No. 11/248,082.
Notice of Allowance dated Apr. 30, 2014 for U.S. Appl. No. 13/688,000.
Notice of Allowance dated Jun. 10, 2013 for U.S. Appl. No. 13/469,849.
Notice of Allowance dated Sep. 9, 2021 for U.S. Appl. No. 11/248,082.
Notice of Allowance dated Sep. 17, 2012 for U.S. Appl. No. 11/248,082.
Notice of Allowance dated Oct. 15, 2010 for U.S. Appl. No. 11/248,082.
Notice of Allowance dated Nov. 22, 2021 for U.S. Appl. No. 14/464,503.
Notice of Allowance dated Nov. 30, 2015 for U.S. Appl. No. 14/464,503.
Office Action dated Jan. 11, 2012 for U.S. Appl. No. 12/188,955.
Office Action dated Feb. 1, 2011 for U.S. Appl. No. 12/879,673.
Office Action dated Mar. 17, 2011 for U.S. Appl. No. 11/248,082.
Office Action dated Mar. 28, 2012 for U.S. Appl. No. 11/248,082.
Office Action dated Mar. 29, 2013 for U.S. Appl. No. 12/188,955.
Office Action dated Mar. 30, 2010 for U.S. Appl. No. 11/248,082.
Office Action dated Apr. 23, 2013 for U.S. Appl. No. 12/188,955.
Office Action dated May 2, 2014 for U.S. Appl. No. 12/188,955.
Office Action dated May 4, 2016 for U.S. Appl. No. 12/188,955.
Office Action dated May 10, 2021 for U.S. Appl. No. 12/188,955.
Office Action dated May 26, 2011 for U.S. Appl. No. 12/188,955.
Office Action dated Jun. 9, 2015 for U.S. Appl. No. 14/464,503.
Office Action dated Jun. 12, 2013 for U.S. Appl. No. 10/595,450,.
Office Action dated Jun. 29, 2009 for U.S. Appl. No. 11/248,082.
AstraTech Healthcare, 'Premimun Wound Drainage Products', http://surgery.astratech.com/Main.aspx?Item-155788&nav=5&nav82118&nava=81296, Copyright ,2010.

(56) References Cited

OTHER PUBLICATIONS

Bard Access Systems, Inc., 'Poly Per-Q-Cath PICC Catheter with Safety Excallibur Introducer', Instructions for Use, , May 2003.
Bard, 'Groshong NXT PICC Instructions for Use', Product Brochure, ,Nov. 2003.
ICU-USA, 'Wound Drainage', www.icu-usa.com/tour/procedures/drains.htm, Copyright 1999-2004
Management of Malignant Pleural Effusions, Am. J. Respir Crit. Care Med., vol. 165 No. 5 ,2000 , 1987-2001.
Pleural Disease—Diagnosis and Management, The Practitioner May 1999 ,412.
Pleurodesis, ASAP, vol. 118, No. 3 ,Sep. 1, 2000 ,577.
Bellamy, et al., The Causes of Death in Conventional Land Warfare: Implications for combat Casualty Care Research, Mil. Med., vol. 149 ,1984 ,55-62.
Bilski, et al., Battlefield Casualties Treated at Camp Rhino, Afghanistan: Lessons Learned, J. Trauma, vol. 54 No. 5 , May 2003 ,814-822.
Campisi, et al., Outpatient Treatment of Spontaneous Pheumothorax in a Community Hospital Using a Heimlich Flutter Valve: A Case Series, The Journal of Emergency Medicine, vol. 15 No. 1 ,1997 ,115-119.
Groves Jr., et al., Operations in Urban Environments, Military Review, vol. 78 No. 4 ,Jul./Aug. 1998.
Heimlich, et al., Valve Drainage of the Pleural Cavity, Diseases of the Chest, vol. 53 No. 3 ,1968 ,282-287.
Hewitt, et al., A Management Strategy for Malignancy-Induced Pleural Effusion: Long-Term horacostomy Drainage, ONF, vol. 14 No. 5 ,1987 ,17-22.
Jaskille, et al., A Portable Handpump is Effective inthe Evacuation of Hemothorax in a Swine Model of Penetratine Chest Injury, The Journal of Trauma Injury, Infection, and Critical Care ,Nov. 2003 ,864-868.
Light,R.W. et al., A Single Intrapleural Injection of Transforming Growth Factor-Beta(2) Produces an Excellent Pleurodesis in Rabbits, Am. J. Respir. Crit. Care Med., vol. 162 No. 1 ,2000 ,98-104.
Light, et al., Talc Slurry is an Effective Pleural Sclerosant in Rabbits, Chest, vol. 106 No. 6 ,1995 ,1702-1706.
Lodi, et al., A New Portable Chest Drainage Device, Ann. Thorac. Surg., vol. 69 ,2000 ,998-1001.
Mabry, et al., United States Army Rangers in Somalia: An Analysis of Combat Casualties on an Urban Battlefield, J. Trauma, vol. 49 No. 3 ,Sep. 2000 ,515-529.
Medcompare, et al., Drains with Reservoirs, General Surgery Product Matrix, Medcompare.com/matrix/1885/Drains-with-Reservoirs.html, Copyright ,2003-2010 ,198-202.
Milton Jr., et al., Urban Operations: Future War, Military Review, vol. 74 Issue 2 ,Feb. 1994.

Office Action dated Jul. 6, 2011 for U.S. Appl. No. 11/248,082.
Office Action dated Jul. 13, 2012 for U.S. Appl. No. 12/188,955.
Office Action dated Jul. 17, 2009 for U.S. Appl. No. 10/595,450.
Office Action dated Jul. 25, 2017 for U.S. Appl. No. 15/081,783.
Office Action dated Aug. 1, 2012 for U.S. Appl. No. 13/469,849.
Office Action dated Aug. 2, 2013 for U.S. Appl. No. 13/688,000.
Office Action dated Aug. 23, 2011 for U.S. Appl. No. 12/879,673.
Office Action dated Sep. 18, 2015 for U.S. Appl. No. 14/464,503.
Office Action dated Oct. 1, 2010 for U.S. Appl. No. 10/595,450.
Office Action dated Oct. 6, 2015 for U.S. Appl. No. 12/188,955.
Office Action dated Oct. 10, 2018 for U.S. Appl. No. 15/912,244.
Office Action dated Oct. 12, 2010 for U.S. Appl. No. 11/535,245.
Office Action dated Oct. 30, 2008 for U.S. Appl. No. 10/595,450.
Office Action dated Oct. 30, 2008 for U.S. Appl. No. 11/248,082.
Office Action dated Oct. 30, 2015 for U.S. Appl. No. 14/162,654.
Office Action dated Nov. 6, 2013 for U.S. Appl. No. 12/188,955.
Office Action dated Dec. 10, 2014 for U.S. Appl. No. 12/188,955.
Office Action dated Dec. 21, 2010 for U.S. Appl. No. 11/248,082.
Office Action dated Dec. 24, 2013 for U.S. Appl. No. 13/688,000.
Office Action dated Jul. 7, 2011 for U.S. Appl. No. 11/535,245.
AstraTech Healthcare, 'Premimun Wound Drainage Products', http://surgery.astratech.com/Main.aspx?Item-155788&navl=5&navl=82118&nava=81296, Copyright ,2010.
Management of Malignant Pleural Effusions, Am. J. Respir. Grit. Care Med., vol. 165 No. 5 ,2000 ,1987-2001.
Hewitt, et al., A Management Strategy for Malignancy-Induced Pleural Effusion: Long-Term Thoracostomy Drainage, ONF, vol. 14 No. 5 ,1987 ,17-22.
Montes, et al., Influence of Talc Dos on Extrapleural Talc Dissemination after Talc Pleurodesis, Am. J. Respir, Grit. Dare Med., vol. 168 No. 3 ,2003 ,348-355.
Ohm, et al., Use of Indwelling Pleural Catheter Compared withThoracoscopic Talc Pleurodesis in the Management of Malignant Pleural Effusions, Division of Thoracic Surgery and Department of Surgery, William Beaumont Hospital, The American Surgeon, vol. 69 ,Mar. 2003 ,198-202.
Pope, et al., Fluid Resuscitation: State fo the Science for Treating Combat Casualties and Civilian Injuries, National Academy Press ,1999.
Schweitzer, et al., Use of Heimlich Valve in compact Autotransfusion Device, The Journal of Trauma, vol. 27 No. 5 ,1987 ,537-542.
Tremblay, et al., Singel-Center Experience with 250 Tunnelled Pleural Catheter Insertions for Manignant Pleural Effusions, Chest, vol. 129 No. 2 ,2006 ,362-368.
Margas, et al., Comparison of Silver Nitrate and Tetracycline as Pleural Sclerosing Agents in Rabbits, Chest, vol. 108 No 4 ,1995 ,1080-1083.
Margas, et al., Experimental Plerueodesis in Rabbits Induced by Silver Nitrate or Talc, ASAP, vol. 199 No. 5 ,May 1, 2001 ,1516.
International Search Report and Written Opinion dated Nov. 30, 2021 for PCT/US2021/045607.

* cited by examiner

US 11,344,318 B2

INFLATABLE RADIAL ARTERY COMPRESSION DEVICE

RELATED APPLICATIONS

This application is a divisional filing of U.S. patent application Ser. No. 15/648,110, filed on Jul. 12, 2017 and titled, Inflatable Radial Artery Compression Device, which claims priority to U.S. Provisional Application No. 62/363,695, filed on Jul. 18, 2016 and titled, Inflatable Radial Artery Compression Device, both of which are hereby incorporated by reference in their entireties.

TECHNICAL FIELD

The present disclosure relates generally to the field of medical devices. More particularly, some embodiments relate to compression devices, including radial artery compression devices with an inflatable chamber.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Numerous medical procedures involve insertion of one or more elongate medical devices into the vasculature of a patient. Some of these interventional procedures involve delivery of a medical device through a radial artery of the patient. Achieving hemostasis during and/or after an interventional procedure that involves puncturing the radial artery may present certain challenges.

To facilitate hemostasis at the radial access site, pressure may be applied slightly upstream of the skin puncture site. Such pressure may prevent or reduce the leakage of blood from the arteriotomy site and promote hemostasis. Certain embodiments described herein facilitate the application of pressure to promote hemostasis at a radial access site.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Thus, two components may be coupled to each other even though they are not in direct contact with each other. For example, two components may be coupled to one another through an intermediate component. The phrase "attached to" refers to interactions between two or more entities which are in direct contact with each other and/or are separated from each other only by a fastener of any suitable variety (e.g., an adhesive). The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a radial artery compression device or a component thereof is the end that is furthest from the attachment point of the arm of the patient during ordinary use of the device. The proximal end refers to the opposite end, or the end nearest the patient during ordinary use. When used as a directional term, the term "radial" refers to the direction pointing from the center of the arm or hand to the thumb-side portion of the arm or hand. The term "ulnar" refers to the opposite direction. The particular volumes recited herein refer to the volumes of fluid that are delivered from a syringe that holds the recited amount of fluid at atmospheric pressure. For example, an inflatable chamber has a capacity of 15 mL if it is capable of receiving 15 mL of air from a syringe that holds 15 mL of air at atmospheric pressure.

Figure 1:
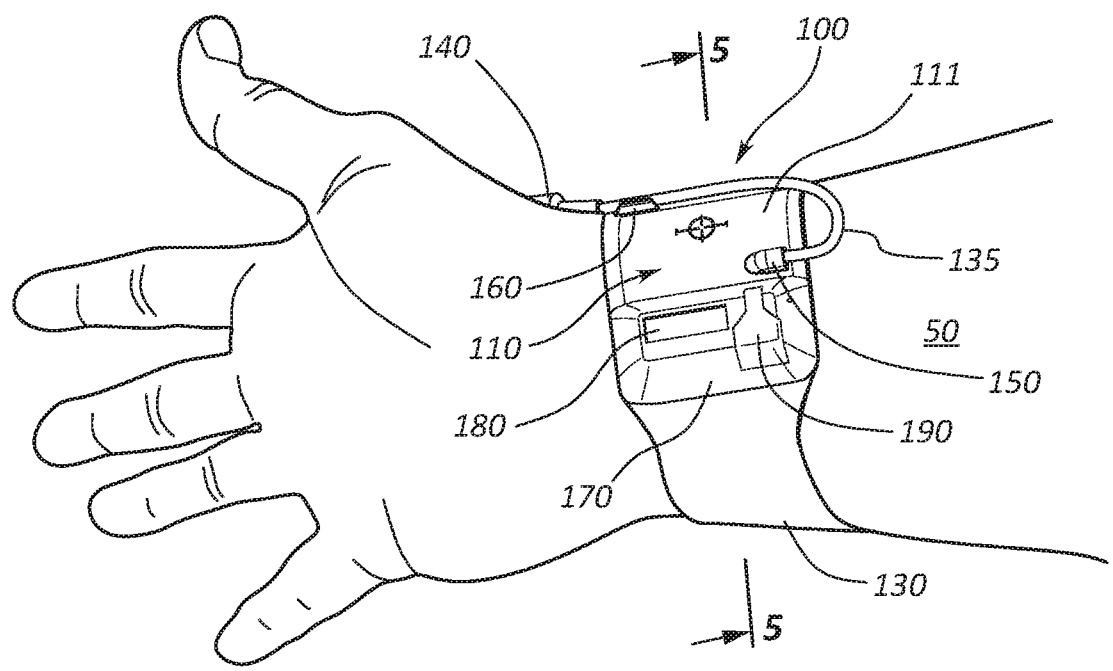
FIG. 1 depicts a radial artery compression device that is secured to a wrist of a patient.
Figure 2:
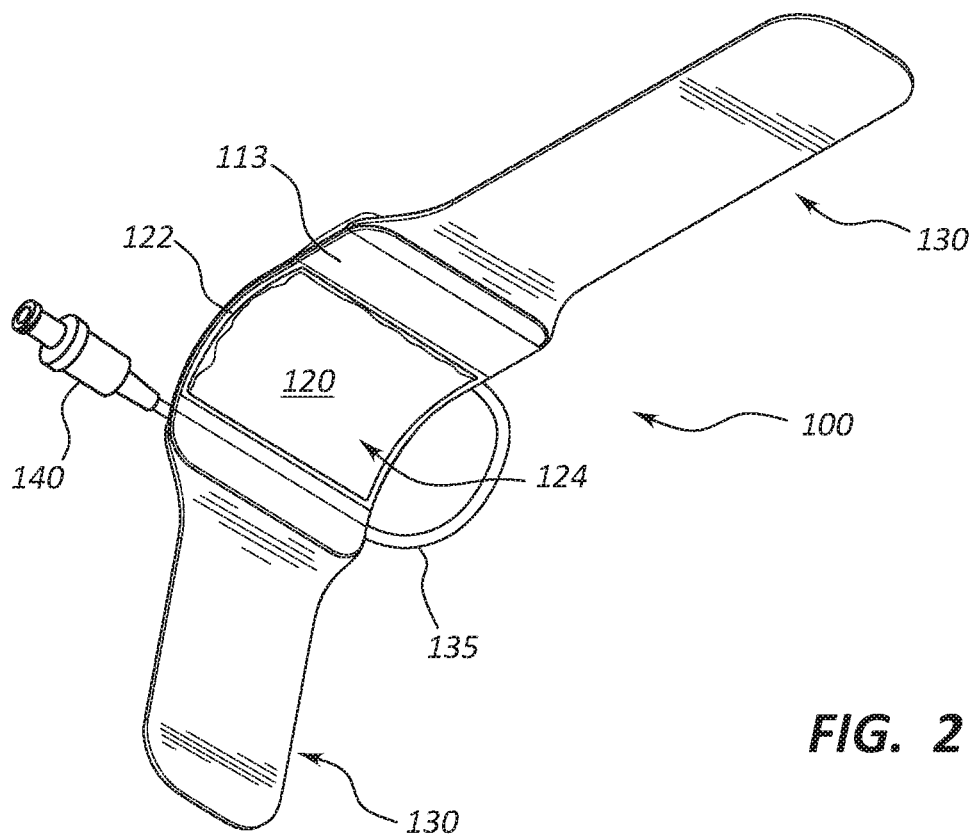
FIG. 2 is a perspective view of an underside of the radial artery compression device of FIG. 1.
Figure 3:
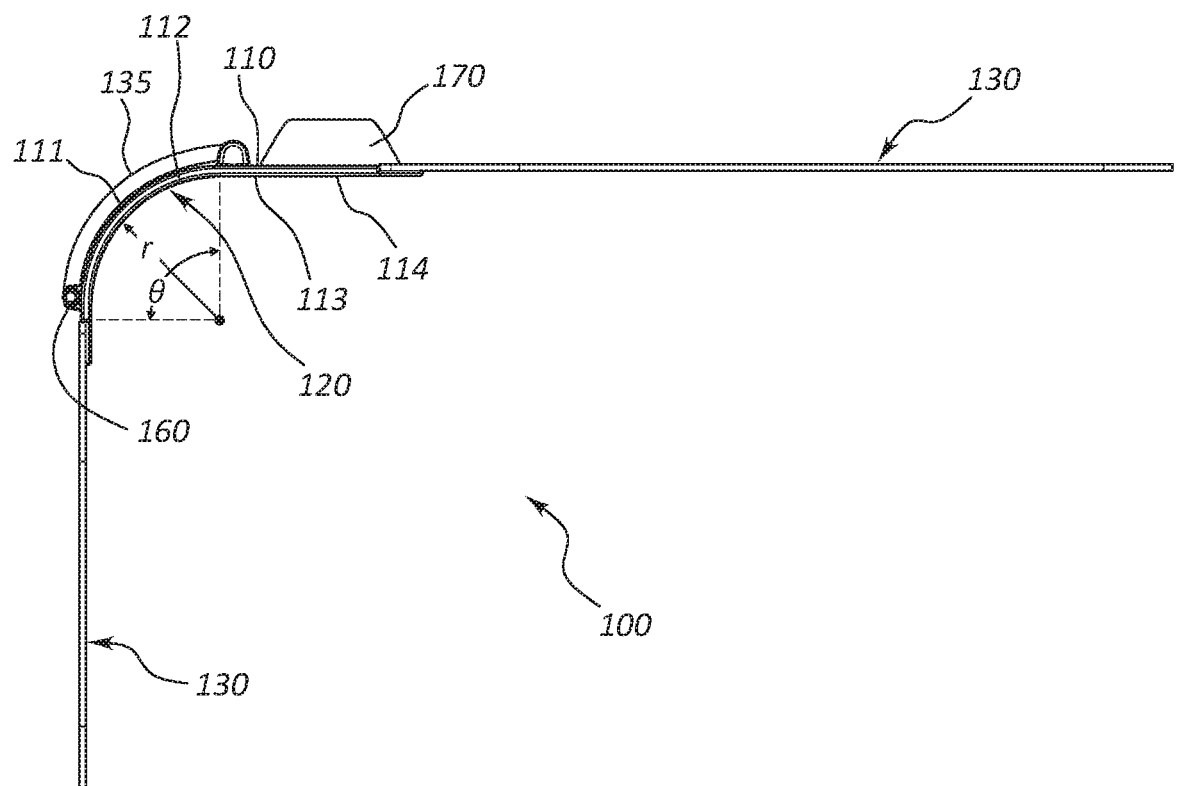
FIG. 3 is a side view of the radial artery compression device of FIGS. 1-2 with the inflatable chamber in an uninflated state.
Figure 4:
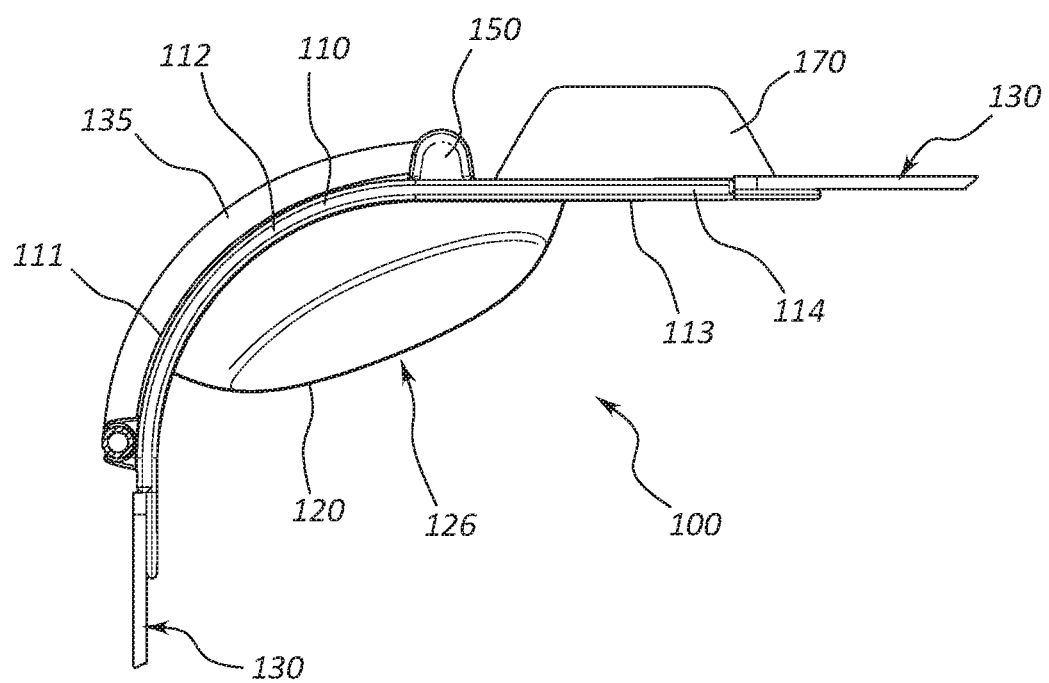
FIG. 4 is a side view of a portion of the radial artery compression device of FIGS. 1-3 with the inflatable chamber in a fully inflated state.
Figure 5:
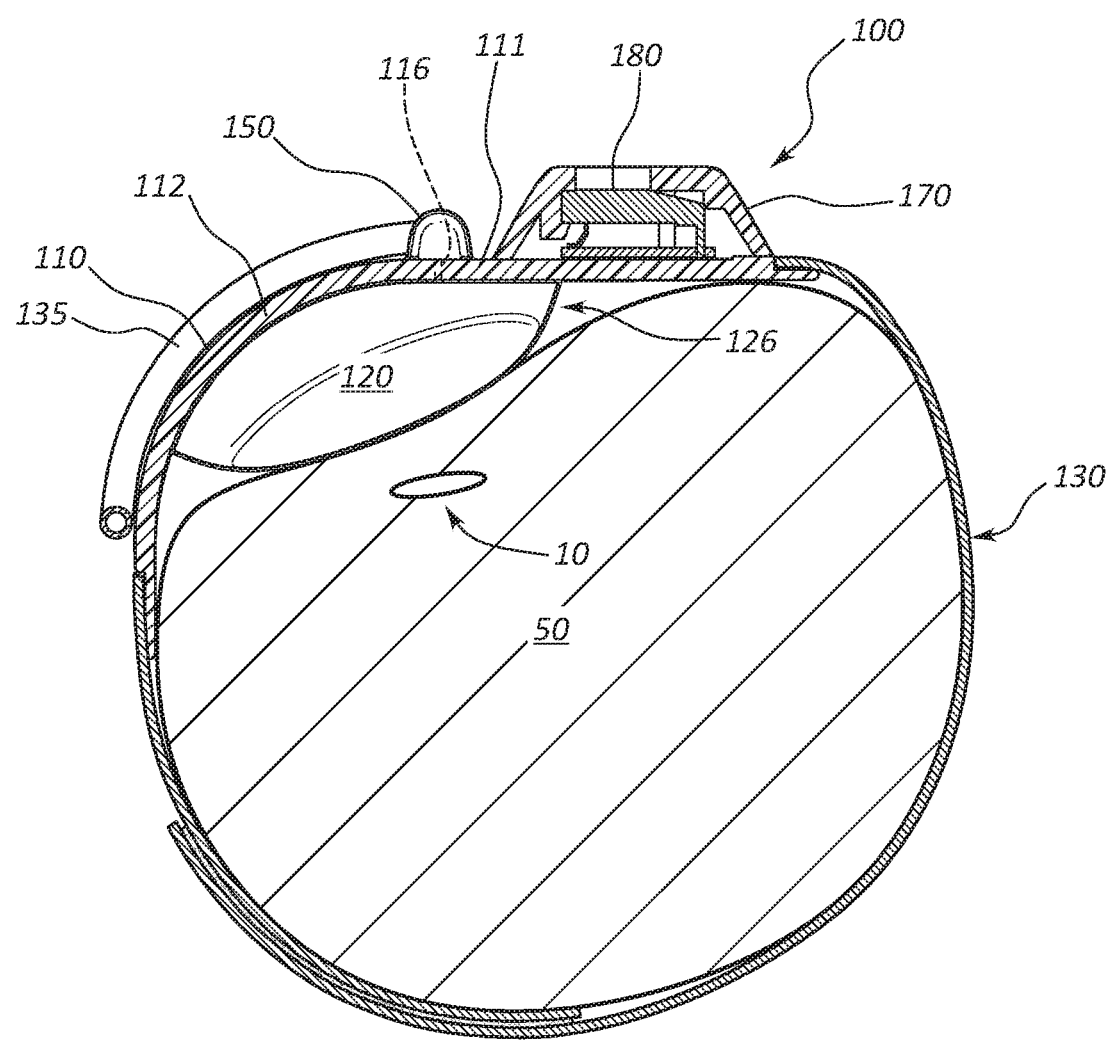
FIG. 5 is a cross-sectional side view of the radial artery compression device of FIGS. 1-4 around the wrist of a patient with the inflatable chamber in a fully inflated state.

FIGS. 1-5 provide alternative views of a radial artery compression device 100. More particularly, FIG. 1 depicts a radial artery compression device 100 secured to the wrist of a patient 50. FIG. 2 provides a perspective view of an underside of the radial artery compression device 100. FIG. 3 provides a side view of the radial artery compression device 100. FIG. 4 provides a side view of the radial artery compression device 100 with an inflatable chamber 126 in an inflated state. And FIG. 5 provides a side view of the radial artery compression device 100 on a wrist of a patient 50 with the inflatable chamber 126 in an inflated state.

As shown in FIGS. 1-5, the radial artery compression device 100 may include a substantially rigid frame 110, a flexible sheet 120, and a wristband 130.

The substantially rigid frame 110 may include an outer surface 111 and an inner surface 113. In some embodiments, the substantially rigid frame 100 is contoured to curve around a thumb-side portion of the wrist of the patient 50. For example, in some embodiments, the substantially rigid frame 110 includes a curved section 112 (see FIGS. 3-5). In the embodiment shown in FIGS. 1-5, the frame 110 is shaped as a curved (e.g., arched) sheet. The outer surface 111 of the frame 110 (or a portion thereof) may be convex, while the inner surface 113 of the frame 110 (or a portion thereof) may be concave. In some embodiments, the substantially rigid frame 110 further includes a substantially straight section 114 configured to be disposed adjacent an underside (i.e., a palmar side) of a wrist of the patient 50. In some embodiments, the substantially rigid frame 110 (or a portion thereof) is transparent.

In some embodiments, the curved section 112 may have a radius of curvature (r) of between 1.5 cm and 2.5 cm (see FIG. 3). Additionally or alternatively, the degree measure (θ) of an arc formed by the curved section 112 may be between 45 and 100 degrees. For example, in some embodiments, the curved section 112 is between 80 and 95 degrees (e.g., approximately 90 degrees).

The flexible sheet 120 may be coupled to the frame 110. For example, in some embodiments, the flexible sheet 120 includes a peripheral portion 122 that is attached to the frame 110 and a central portion 114 that is not attached to the frame 110. In some embodiments, the peripheral portion 122 of the flexible sheet 120 is attached to the frame 110 via welding or an adhesive. The flexible sheet 120 may be made from any suitable material, such as polyurethane or PVC. In some embodiments, the material of the flexible sheet is stretchable. In the depicted embodiment, the flexible sheet is substantially rectangular in shape, although other shapes are also within the scope of this disclosure. In some embodiments, the flexible sheet 120 (or a portion thereof) is transparent. For example, in some embodiments, both the substantially rigid frame 110 (or a portion thereof) and the flexible sheet 120 (or a portion thereof) are transparent, thereby allowing a practitioner to view a radial access site through the frame 110 and the flexible sheet 120. In some embodiments, the practitioner may need to view through only two layers (e.g., the frame 110 and the flexible sheet 120) to view the radial access site. Viewing through only two layers may provide improved visual clarity relative to embodiments in which the radial access site is viewed through more than two layers or parts.

The wristband 130 may be coupled to the frame 110. For example, the wristband 130 may include a first strap that is attached to one side of the frame 110 and a second strap that is attached to an opposite side of the frame 110. The wristband 130 may be configured to secure the frame 110 adjacent to the wrist of the patient 50. In some embodiments, the entire wristband 130 (or a portion thereof) is opaque. In some embodiments, the wristband 130 is colored and/or decorated. In some embodiments, the wristband 130 includes hook and loop fasteners (e.g., Velcro). For example, in some embodiments, the wristband 130 is an integrated Velcro strap. In other embodiments, other attachment means are used to secure the radial artery compression device 100 to the arm of the patient 50.

The substantially rigid frame 110 and the flexible sheet 120 may form the inflatable chamber 126. For example, the inner surface 113 of the frame 110 and the flexible sheet 120 may at least partially define the inflatable chamber 126. Stated differently, a wall of the inflatable chamber 126 may be defined by the frame 110. In this fashion, the inflatable chamber 126 may be defined by both a first portion (e.g., the substantially rigid frame 110) of the radial artery compression device 100 that does not change size or shape as the inflatable chamber 126 is inflated and a second portion (e.g., the flexible sheet 120) of the radial artery compression device 100 that does change in size or shape as the inflatable chamber 126 is inflated.

When the wristband 130 is secured to the wrist of the patient 50, the inflatable chamber 126 may be positioned adjacent to a radial artery 10 of the patient (see FIG. 5). In some embodiments, the radial artery compression device 100 includes only a single inflatable chamber 126. The use of the single inflatable chamber 126 may provide one or more advantages relative to radial artery compression devices that employ multiple inflatable chambers, such as ease of construction and/or ease of use. In some embodiments, the maximum capacity of the inflatable chamber is between 3 mL and 30 mL. For example, in some embodiments, the maximum capacity of the inflatable chamber 126 is between 3 mL and 12 mL, between 3 mL and 20 mL, between 3 mL and 25 mL, between 5 mL and 15 mL, between 10 mL and 20 mL, between 10 mL and 30 mL, or between 15 mL and 30 mL. The inflatable chamber 126 may be configured for applying varying amounts of pressure to a radial access site of the patient 50. In some embodiments, the inflatable chamber 126 provides pressure to the radial access site in a manner that avoids restricting the ulnar artery.

In some embodiments, the radial artery compression device 100 includes tubing 135 that extends from a first aperture 116 (see FIG. 5) in the substantially rigid frame 110 to a valve 140. The tubing 135 and the valve 140 may be in fluid communication with the inflatable chamber 126 that is formed by the substantially rigid frame 110 and the flexible sheet 120. In some embodiments, the valve 140 is configured to allow fluid to flow through the valve 140 when the valve 140 is coupled to an inflation device (e.g., a syringe), but prevents fluid flow through the valve 140 when the valve 140 is not coupled (i.e., detached from) the inflation device. In other words, the valve 140 may maintain a positive fluid pressure within the inflatable chamber 126 after the inflation device has been uncoupled from the valve 140.

In the depicted embodiment, the tubing 135 is coupled to the frame 110 via a connector 150 that protrudes from the outer surface 111 of the frame 110. In some embodiments, the tubing 135 extends from the connector 150 for a length of 5 cm to 15 cm, 6 cm to 15 cm, 8 cm to 15 cm, 10 cm to 15 cm, 12 cm to 15 cm, 6 cm to 12 cm, 6 cm to 10 cm, 6 cm to 8 cm, or 8 cm to 10 cm in length. In other words, in some embodiments, the tubing 135 is between about 5 cm to about 15 cm. In other embodiments, no tubing 135 is used. In other embodiments, the tubing 135 is of some other length.

In some embodiments, the radial artery compression device 100 may further include a retainer 160 (e.g., a clip) that is configured to secure a free end of the tubing 135 to the frame 110. In some embodiments, when the radial artery compression device 100 is secured to the right arm of the patient 50, the retainer 160 may be positioned (1) ulnar or radial of the connector 150 and/or (2) proximal or distal of the connector 150. For example, when the depicted embodiment is secured to the right arm of the patient 50 as shown in FIG. 1, the retainer 160 is positioned radial of and distal of the connector 150. The retainer 160 and the connector 150 may be positioned at a distance from one another such that, when a proximal end of the tubing 135 is attached to the retainer 160, only a small length of the tubing 135 protrudes from the radial artery compression device 100, thereby minimizing the bulk of the radial artery compression device 100.

Figure 6:
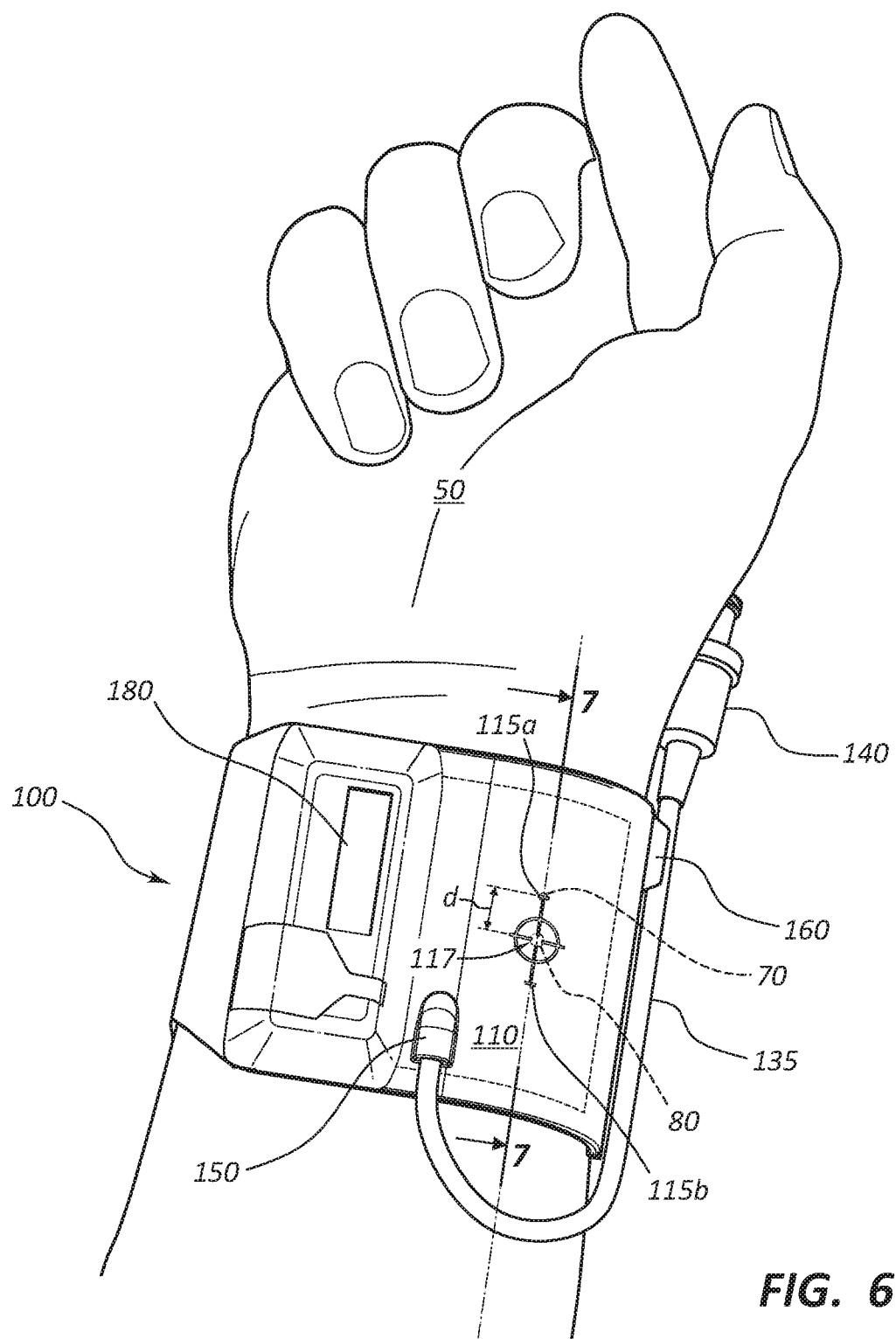
FIG. 6 is a perspective view of the radial artery compression device of FIGS. 1-5 showing the relative positioning of indicia to a puncture site and an arteriotomy site.
Figure 7:
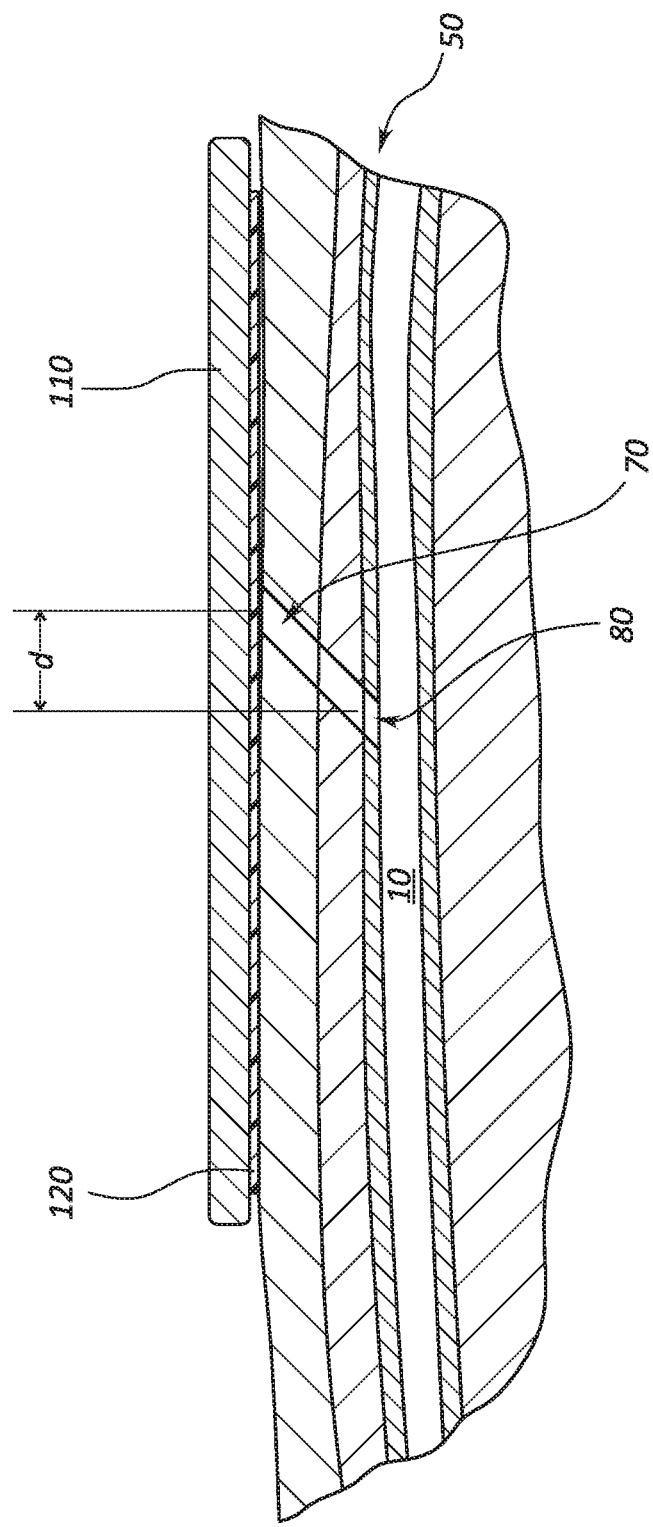
FIG. 7 is a cross-sectional view of the radial artery compression device of FIGS. 1-6 showing a puncture site and an arteriotomy site.

FIGS. 6 and 7 show one way of positioning the radial artery compression device 100 relative to a puncture site 70 and an arteriotomy site 80. More particularly, FIG. 6 shows the radial artery compression device 100 secured to the wrist of the patient 50 at a particular location relative to the puncture site 70, while FIG. 7 provides a cross-sectional view of the through plane 7-7 of FIG. 6.

When an elongate device, such as a needle, sheath, or catheter, is introduced into the radial artery 10 for an interventional procedure, the elongate device may be inserted at an angle such that the location where the elongate device passes through the skin (i.e., the puncture site) is not directly above the location where the elongate device passes through the artery wall (i.e., the arteriotomy site). In other words, the puncture site may be separated from the arteriotomy site by a distance (d). In some embodiments, the distance (d) is approximately 1-10 mm, 2-5 mm, and/or 3-4 mm.

In some circumstances, it may be advantageous to focus compression on the arteriotomy site 80 rather than the puncture site 70. In other words, hemostasis may be more rapidly and effectively achieved by applying a compression force to the arteriotomy site 80 in a relatively direct manner. To assist a practitioner in placing the radial artery compression device 100 at a location that provides appropriate compression to the arteriotomy site 80, the radial artery compression device 100 may include indicia on the frame 110. The indicia on the frame 110 may be designed to facilitate identification of the arteriotomy site 80 relative to the visible puncture site 70 in the skin of the patient 50.

For example, in the depicted embodiment, a first indicium 115a is disposed on the frame 110. In the depicted embodiment, the first indicium 115a is located at the intersection of a T-shaped mark on the frame 110. When the first indicium 115a is aligned with the puncture site 70 that is visible through the transparent frame 110 and the transparent flexible sheet 120, a second indicium 117 is disposed directly over the (non-visible) arteriotomy site 80. In the depicted embodiment, the second indicium 117 is the center of a target-shaped mark on the frame 110. In some embodiments, the second indicium 117 is disposed directly above a center of the flexible sheet 120. Stated differently, the second indicium 117 may be disposed directly over a region of the inflatable chamber 126 that is designed to extend furthest from the frame 110 when the inflatable chamber 126 is in an inflated state.

In some embodiments, the radial artery compression device 100 may additionally or alternatively include an indicium 115b. The indicium 115b may be aligned with a puncture site when the radial artery compression device 100 is placed on the left hand of the patient 50. Stated differently, in some embodiments, the radial artery compression device 100 may include indicia to facilitate alignment with the puncture site 70 regardless of the arm on which the radial artery compression device 100 is placed. One of ordinary skill in the art will recognize that indicia that differ in some ways from the indicia shown in FIG. 6 may be used for analogous purposes. In other words, various forms of indicia may be used to facilitate proper alignment of the radial artery compression device 100.

In some embodiments, the radial artery compression device 100 may include one or more of the following components: a pressure sensor, a timer, an alarm, a control unit, a power source, a wireless connection, and a display 180. In some embodiments, one or more of these components are enclosed within and/or supported by a housing 170. The housing 170 may be fixedly or detachably coupled to the frame 110. For example, in the depicted embodiment, the housing 170 is fixedly coupled to and extends from the frame 110. In embodiments in which the housing 170 is detachably coupled to the frame, the housing 170 and/or one or more components disposed therein (e.g., a pressure sensor, a timer, an alarm, a control unit, a power source, a wireless connection, or a display 180) may be reprocessed and/or refurbished for further use.

In some embodiments that include a pressure sensor or pressure transducer (not shown), the pressure sensor may be in fluid communication with the inflatable chamber 126. For example, the pressure sensor may be in fluid communication with the inflatable chamber 126 through a second aperture (not shown) in the substantially rigid frame 110. The pressure within the inflatable chamber 126, as measured by the pressure sensor, may inform protocols for use of the radial artery compression device 100. For example, pressure measurements obtained by the pressure sensor may be relayed to the display 180. The practitioner may use the pressure information on the display to increase or decrease the amount of fluid within the inflatable chamber 126 as desired. In some embodiments, the pressure sensor is detachable from the remaining portions of the radial artery compression device 100. In other embodiments, the pressure transducer is not detachable from the radial artery compression device 100.

As noted above, some radial artery compression devices include a timer. In some embodiments, the timer is a countdown timer. In other or further embodiments, the timer is a stopwatch (i.e., count-up) timer. The timer may be configured to measure time from some reference period, such as when an actuator (e.g., a button or pull tab) is actuated. In some embodiments, time is measured from when the radial artery compression device 100 is positioned on the arm of the patient 50 and initially inflated. The timer may additionally or alternatively measure time from when fluid is initially removed from the inflatable chamber 126 during deflation. In some embodiments, the timer may be configured to measure the amount of time that the inflatable chamber 126 has remained at a particular pressure.

In some instances, the timer may be in communication with the display 180. In some embodiments, the display 180 shows the amount of elapsed time in minutes and seconds. In other or further embodiments, the display may show the amount of elapsed time in hours and minutes. In some embodiments, the display may transition from displaying minutes and seconds to displaying hours and minutes once the amount of elapsed time reaches one hour. In some embodiments, the timer is detachable from the remaining portions of the radial artery compression device 100. In other embodiments, the timer is not detachable.

In some embodiments, the radial artery compression device 100 includes an alarm. In some cases, the alarm may be a visible alarm (e.g., the flashing of light-emitting diodes). In other or further embodiments, the alarm may be audible. The alarm may alert the patient 50 and/or the practitioner to certain information (e.g., the length of the time that the radial artery compression device 100 has remained in a particular state). Based on this information, the practitioner and/or the patient 50 may make any needed changes.

In some embodiments, the radial artery compression device 100 may include a wireless connection (e.g., via Bluetooth or Wi-Fi). Information from the radial artery compression device 100 (e.g., information relating to pressure or elapsed time) may be wirelessly transmitted to one of more other devices to alert a medical practitioner of treatment needs, such as the need to modify the amount of pressure provided to the radial artery at a particular time.

The radial artery compression device 100 may be used at or near the conclusion of a medical procedure to facilitate hemostasis of the radial artery 10. For example, in some procedures, the radial artery compression device 100 may be secured to the wrist of the patient 50, such as via the wristband 130. The practitioner may secure the radial artery compression device 100 to the wrist of the patient 50 such that the inflatable chamber 126 of the radial artery compression device 100 is positioned adjacent to a radial access site. For example, in some embodiments, the radial artery compression device 100 is placed on the wrist around a portion of an elongate medical instrument that accesses the radial artery of the patient 50 through a radial access site.

In some circumstances, the practitioner may align the first indicium 115a on the frame 110 of the radial artery compression device 100 with the puncture site 70 in the skin of the patient 50. For example, the practitioner may view the radial access site through the frame 110 and the flexible sheet 120 and align the first indicium 115a on the frame 110 with the puncture site 70. When the first indicium 115a is aligned with the puncture site 70, the inflatable chamber 126 of the radial artery compression device 100 may be positioned to provide compression to the arteriotomy site 80 that is upstream of the puncture site 70. Stated differently, when the first indicium 115a of the radial artery compression device 100 is aligned with the puncture site 70 in the skin of the patient 50, the inflatable chamber 126 may be positioned directly over an arteriotomy site of the patient 50. In some embodiments, the second indicium 117 is disposed directly over the arteriotomy site 80 when the first indicium 115a is aligned with the puncture site 70.

Once the radial artery compression device 100 is properly placed on the arm of the patient 50, the inflatable chamber 126 may be inflated in any suitable manner. For example, in some embodiments, the practitioner may connect an inflation device (e.g., a syringe) to the valve 140. Connecting the inflation device to the valve 140 may open the valve 140, allowing the practitioner to deliver fluid into the inflatable chamber 126. For example, a practitioner may advance a plunger of a syringe that is connected to the valve 140, causing fluid to pass through the valve 140, the tubing 135, and the first aperture 116 to enter into the inflatable chamber 126. The delivery of fluid to the inflatable chamber 126 may cause the inflatable chamber 126 to expand, thereby increasing the amount of pressure that is applied to the radial access site. Stated differently, inflating the inflatable chamber 126 may increase pressure that is applied to the radial access site.

In some circumstances, the inflatable chamber 126 may first be partially inflated to provide some compression force to the radial access site. With the inflatable chamber 126 in a partially inflated state, an elongate medical device that is partially inserted into the radial artery may be withdrawn from the radial artery such that no medical device extends through the puncture site 70 of the skin of the patient 50 to the arteriotomy site 80.

After the elongate medical device has been removed, fluid may then be delivered to the inflatable chamber 126 in an amount that is sufficient to stop bleeding at the arteriotomy site 80. For example, in some embodiments, sufficient fluid may be provided to fully inflate the inflatable chamber 126. Once enough fluid has been delivered to the inflatable chamber 126 to stop the bleeding, fluid within the inflatable chamber 126 may be slowly withdrawn until a flash of blood is visible at the skin puncture site 70 through the frame 110 and the flexible sheet 120. At this stage, additional fluid (e.g., 1-2 mL) may be injected back into the inflatable chamber 126 to stop the bleeding. This process may provide adequate pressure to achieve hemostasis while maintaining patency of the radial artery 10. In other words, this protocol can be used to ensure that sufficient pressure is provided to prevent bleeding, while avoiding the application of excessive force (which can unduly restrict blood flow through the radial artery 10).

As the arteriotomy site 80 and/or the puncture site 70 begin to heal, the amount of compression needed to maintain hemostasis may decrease. Accordingly, the practitioner may deflate the inflatable chamber 126 over a series of stages. Such deflation may follow a particular predetermined protocol. For example, in some embodiments, after the radial artery compression device 100 has been used to apply a compressive force for some period of time (e.g., 5 minutes to 5 hours), a predetermined volume (e.g., 0.5 mL to 3 mL) of fluid may be removed every 2-3 minutes until all of the air is removed. Provided that the removal of compression force does not result in further bleeding, the radial artery compression device 100 may then be removed from the patient 50. In other words, once compression is no longer needed to ensure hemostasis, the radial artery compression device 100 may be removed from the patient 50.

In some instances, fluid may be removed from the inflatable chamber 126 based on information provided by the radial artery compression device 100. For example, in some embodiments, the inflatable chamber 126 may be deflated based on information obtained from a timer or an alarm of the radial artery compression device 100. For example, the radial artery compression device may count the amount of time that has elapsed since the radial artery compression device 100 was placed on the patient 50 and alert the practitioner of the proper time to begin removing fluid from the inflatable chamber 126. The timer may be activated by an actuator, such as a button or a pull tab. In some embodiments, the timer may count up. In other or further embodiments, the timer may count down. The radial artery compression device 100 may also indicate the timing for staged deflation. In some instances, the practitioner or the patient 50 is alerted to the need to remove fluid based on a visible indicator (e.g., information provided on the display 180). The information from the visible indicator may be provided on the display 180, via lights (e.g., light-emitting diodes), or in some other manner. In other or further embodiments, the practitioner or the patient 50 is alerted to the need to remove fluid based on one or more sounds (e.g., the sounds of an audible alarm) that are emitted from the radial artery compression device 100. In some embodiments, lights (e.g., LEDs) or other indicia inform the practitioner of the stage of deflation. For example, in some embodiments, lights may be used to indicate the number of times fluid has been removed from the inflatable chamber 126.

Figure 8:
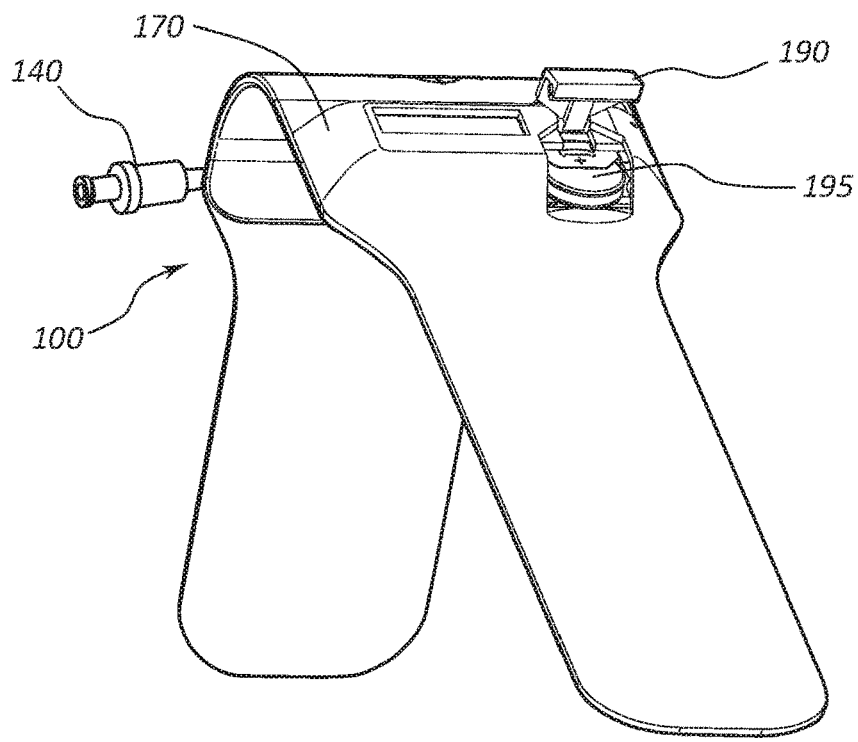
FIG. 8 is a perspective view of the radial artery compression device of FIGS. 1-7 showing a battery removal mechanism.

The radial artery compression device 100 may be powered by any suitable power source. For example, in the embodiment depicted in FIGS. 1-8, the radial artery compression device 100 includes a battery 195 that is disposed within the housing 170. The battery 195 may provide power to a pressure sensor, a timer, an alarm, and/or the display 180. In some embodiments, the radial artery compression device 100 is configured to facilitate removal of the battery from the housing. For example, the radial artery compression device 100 may include a battery latch 190 that is rotatably coupled to the housing 170. The battery latch 190 may be opened as shown in FIG. 8 to remove the battery 195 from the radial artery compression device 100. In other words, the radial artery compression device 100 may be configured to facilitate removal of one or more batteries 195 for the housing 170. Facile removal of the battery 195 may allow the radial artery compression device 100 to be discarded separate from battery waste.

Figure 9:
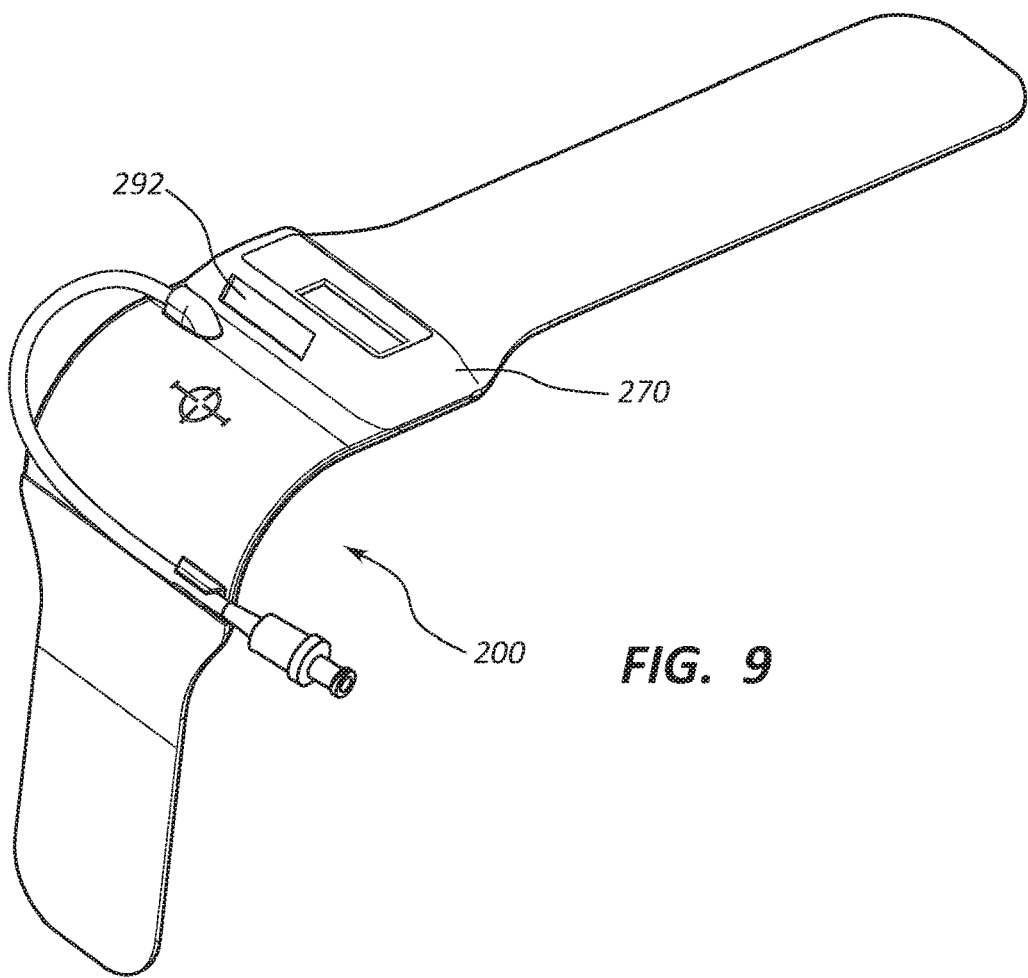
FIG. 9 is a perspective view of a solar-powered radial artery compression device.

Radial artery compression devices need not be powered by one or more batteries. For example, FIG. 9 provides a perspective view of a radial artery compression device 200 that includes a solar panel 292 that is supported by a housing 270. The radial artery compression device 200 may use solar energy to power components such as a pressure sensor, a timer, an alarm, lights, and/or a display. Alternatively, some radial artery compression devices may be powered by a slow-discharge capacitor. The use of a slow-discharge capacitor may allow the radial artery compression device to be discarded without concern for battery waste. In still other embodiments (e.g., embodiments lacking components such as a pressure sensor, a timer, an alarm, lights, and a display), the radial artery compression device may not include a power source within the housing.

Figure 10:
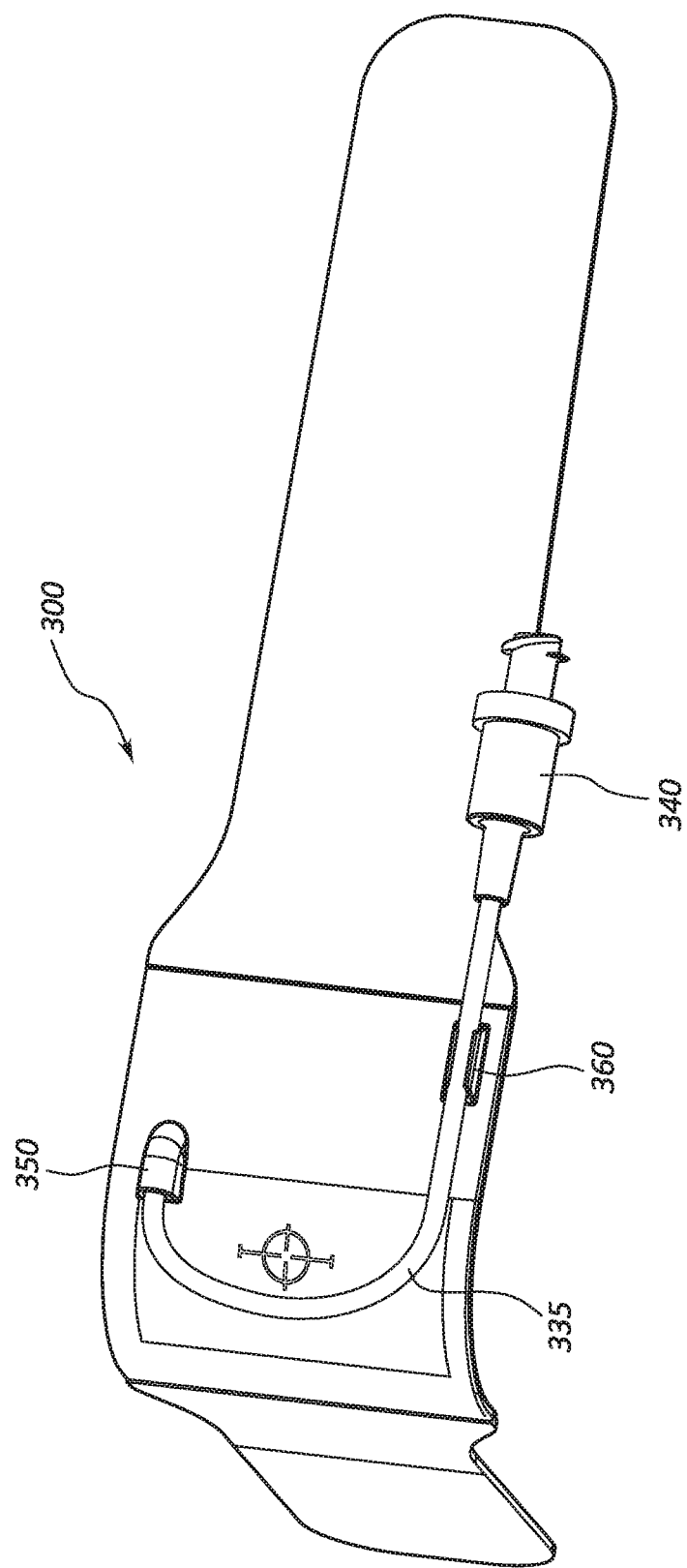
FIG. 10 is a perspective view of another embodiment of a radial artery compression device.

FIG. 10 provides a perspective view of another radial artery compression device 300. The radial artery compression device 300 is generally analogous to the radial artery compression devices 100, 200 described above. However, in the embodiment shown in FIG. 10, the connector 350 and the retainer 360 are positioned in different locations when compared to the connectors and retainers shown in FIGS. 1-9.

When the radial artery compression device 300 is disposed on the right wrist of a patient for placement over a radial artery, the connector 350 is both proximal and radial of the retainer 360. Tubing 335 may initially extend radially from the connector 350 and then bend such that a valve 340 at the free end of the tubing is disposed ulnar of the connector 350. The retainer 360 may secure the tubing 335 adjacent to the remaining portions of the radial artery compression device 300.

Some radial artery compression devices described herein, such as radial artery compression devices 100, 200, and 300 may be placed on either arm of the patient 50. For example, while the radial artery compression device 100 is shown in FIG. 1 on the right arm of the patient 50, the radial artery compression device 100 may alternatively be used on the left arm of the patient 50. When the radial artery compression device 100 is disposed on the left arm of the patient 50, the frame 110 may be contoured to curve around a thumb-side portion of the left wrist of the patient 50. Stated differently, when the radial artery compression device 100 of FIG. 1 is properly placed on the left arm of the patient 50, the radial artery compression device 100 of FIGS. 1-8 may be rotated such that the connector 150 is both ulnar of and distal of the retainer 160.

While the compression devices described above are described as radial artery compression devices, some compression devices may, additionally or alternatively, be suitable for compression of an ulnar artery. For example, a compression device may be placed on the patient such that the frame curves around the ulnar side of the wrist. When placed on the patient in this manner, the inflatable chamber may be positioned adjacent to the ulnar artery such that inflation of the inflatable chamber applies pressure to an access site in the ulnar artery. Thus, some compression devices described herein may be used to promote healing at access sites in an ulnar artery.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A method for achieving hemostasis at an access site of a radial artery, the method comprising: providing a radial artery compression device, the device comprising: an inflatable chamber; a substantially rigid frame; and a wristband; securing the radial artery compression device to a wrist of a patient such that the inflatable chamber of the radial artery compression device is positioned adjacent to the access site of the radial artery; aligning an indicium on the frame with a puncture site in the access site to identify a location in the access site, wherein said location is an arteriotomy site axially separated from the puncture site; and inflating the inflatable chamber to increase pressure that is applied to the access site at the arteriotomy site; wherein the access site is visible through the frame and the inflatable chamber.

2. The method of claim 1, wherein a wall of the inflatable chamber is defined by the frame.

3. The method of claim 1, further comprising removing air from the inflatable chamber over a plurality of stages according to a predetermined protocol.

4. The method of claim 3, further comprising activating a timer on the device.

5. The method of claim 4, wherein the predetermined protocol correlates to indicia on the timer.

6. The method of claim 1, further comprising positioning a curved portion of the frame around a thumb-side portion of the patient's wrist.

7. The method of claim 1, further comprising opening a valve in fluid communication with the inflatable chamber.

8. The method of claim 7, wherein opening the valve comprises coupling an inflation device to the valve such that the inflation device actuates the valve.

9. The method of claim 1, further comprising coupling an inflation device to tubing in fluid communication with the inflatable chamber.

10. The method of claim 9, further comprising coupling a free end of the tubing to a retainer on the frame.

11. A method for achieving hemostasis at an access site of a radial artery, the method comprising:
- positioning a first indicium on a radial artery compression device over a puncture site on a patient's skin so that a second indicium indicates an arteriotomy site axially separated from the puncture site; and
- inflating an inflatable chamber on the device while the first indicium is positioned over the puncture site such that the inflatable chamber compresses an arteriotomy site.

12. The method of claim 11, further comprising viewing the puncture site through a frame of the device.

13. The method of claim 12, further comprising viewing the puncture site through a portion of the inflatable chamber.

14. The method of claim 11, further comprising simultaneously viewing the first indicium and the puncture site without displacing the device.

15. The method of claim 11, wherein positioning the first indicium over the puncture site also positions a compression portion of the inflatable chamber over the arteriotomy site.

* * * * *

UNITED STATES PATENT AND TRADEMARK OFFICE
CERTIFICATE OF CORRECTION

PATENT NO. : 11,344,318 B2
APPLICATION NO. : 16/921343
DATED : May 31, 2022
INVENTOR(S) : Lampropoulos et al.

It is certified that error appears in the above-identified patent and that said Letters Patent is hereby corrected as shown below:

In the Claims

Claim 11, Column 11, Line 14 reads: ...compresses an arteriotomy
And should read: ...compresses the arteriotomy Signed and Sealed this
Twentieth Day of June, 2023

Katherine Kelly Vidal
Director of the United States Patent and Trademark Office